US00RE44127E

(19) United States
(12) Reissued Patent
Moncrief et al.

(10) Patent Number: US RE44,127 E
(45) Date of Reissued Patent: Apr. 2, 2013

(54) SYSTEM AND SOFTWARE OF ENHANCED PHARMACEUTICAL OPERATIONS IN LONG-TERM CARE FACILITIES AND RELATED METHODS

(75) Inventors: James W. Moncrief, Plano, TX (US); James J. Martin, Spring, TX (US)

(73) Assignee: Tech Pharmacy Services, Inc., Dallas, TX (US)

(21) Appl. No.: 13/429,269

(22) Filed: Mar. 23, 2012

Related U.S. Patent Documents

Reissue of:
(64) Patent No.: 7,685,004
Issued: Mar. 23, 2010
Appl. No.: 11/951,050
Filed: Dec. 5, 2007

U.S. Applications:
(63) Continuation of application No. 10/944,993, filed on Sep. 20, 2004, now Pat. No. 7,698,019.

(60) Provisional application No. 60/516,678, filed on Nov. 3, 2003.

(51) Int. Cl.
*G06Q 50/00* (2006.01)
*G06Q 40/00* (2006.01)

(52) U.S. Cl. ..... 705/2; 705/4
(58) Field of Classification Search ..... 705/2–4
See application file for complete search history.

(56) References Cited

U.S. PATENT DOCUMENTS

| | | | |
|---|---|---|---|
| 3,917,045 | A | 11/1975 | Williams et al. |
| 4,054,343 | A | 10/1977 | Heyland |
| 4,546,901 | A | 10/1985 | Buttarazzi |
| 4,839,806 | A | 6/1989 | Goldfischer et al. |
| 4,847,764 | A | 7/1989 | Halvorson |
| 5,014,875 | A | 5/1991 | McLaughlin et al. |
| 5,082,113 | A | 1/1992 | Romick |
| 5,084,828 | A | 1/1992 | Kaufman et al. |
| 5,102,008 | A | 4/1992 | Kaufman et al. |
| 5,148,944 | A | 9/1992 | Kaufman et al. |
| 5,197,632 | A | 3/1993 | Kaufman et al. |
| 5,230,441 | A | 7/1993 | Kaufman et al. |
| 5,263,596 | A | 11/1993 | Williams |
| 5,267,174 | A | 11/1993 | Kaufman et al. |
| 5,329,459 | A | 7/1994 | Kaufman et al. |
| 5,335,816 | A | 8/1994 | Kaufman et al. |
| 5,405,048 | A | 4/1995 | Rogers et al. |

(Continued)

FOREIGN PATENT DOCUMENTS

| | | |
|---|---|---|
| WO | 02/21402 A1 | 3/2002 |
| WO | WO0221402 | 3/2002 |

OTHER PUBLICATIONS

Notice of Allowance for U.S. Appl. No. 11/818,416 dated Mar. 26, 2012, 9 pages.

(Continued)

*Primary Examiner* — Robert Morgan
*Assistant Examiner* — Robert Sorey
(74) *Attorney, Agent, or Firm* — Bracewell & Giuliani, LLP

(57) ABSTRACT

A system, pharmacy management software, and related methods of enhanced pharmaceutical operations in patient care facilities are provided. The pharmacy management software, for example, can include instructions that when executed by a computer, cause the computer to perform the operations of providing instructions to pharmaceutical storage and electronic dispensing carts positioned at various patient care facilities according to patient specific prescription requirements, receiving dispensing data from each of the carts, and providing separate billing records including billing data indexed by reimbursement provider for each patient at the patient care facilities. The operations can also include consolidating the billing data by patient, by patient care facility, by remote pharmacy, and/or consolidating billing data by reimbursement provider, and submitting separate consolidated reimbursement claims electronically to each respective reimbursement provider.

28 Claims, 16 Drawing Sheets

U.S. PATENT DOCUMENTS 5,480,062 A 1/1996 Rogers et al.
5,489,025 A 2/1996 Romick
5,490,610 A 2/1996 Pearson
5,562,232 A 10/1996 Pearson
5,564,593 A 10/1996 East, Sr.
5,597,995 A 1/1997 Williams et al.
5,611,038 A 3/1997 Shaw et al.
5,612,890 A 3/1997 Strasser et al.
5,623,242 A 4/1997 Dawson, Jr. et al.
5,641,093 A 6/1997 Dolin et al.
RE35,743 E 3/1998 Pearson
5,761,877 A 6/1998 Quandt
5,842,976 A 12/1998 Williamson
5,845,253 A 12/1998 Rensimer
5,883,806 A 3/1999 Meador et al.
5,907,493 A 5/1999 Boyer et al.
5,933,809 A 8/1999 Hunt et al.
5,945,651 A 8/1999 Chorosinski et al.
5,963,136 A 10/1999 O'Brien
5,963,453 A 10/1999 East
5,970,462 A 10/1999 Reichert
5,971,594 A 10/1999 Sahai et al.
6,004,020 A 12/1999 Bartur
6,011,999 A 1/2000 Holmes
6,021,392 A 2/2000 Lester et al.
6,032,155 A 2/2000 De la Huerga
6,067,524 A 5/2000 Byerly et al.
6,116,461 A 9/2000 Broadfield et al.
6,154,726 A 11/2000 Rensimer
6,175,779 B1 1/2001 Barrett
6,202,923 B1 3/2001 Boyer et al.
6,208,973 B1 3/2001 Boyer et al.
6,219,587 B1 4/2001 Ahlin et al.
6,240,394 B1 5/2001 Uecker et al.
6,259,654 B1 7/2001 De la Huerga
6,263,259 B1 7/2001 Bartur
6,289,656 B1 9/2001 Wangu et al.
6,304,797 B1 10/2001 Shusterman
6,308,109 B1 10/2001 Yuyama et al.
6,330,491 B1 12/2001 Lion
6,332,100 B1 12/2001 Sahai et al.
6,338,007 B1 1/2002 Broadfield et al.
6,354,783 B1 3/2002 Stoy et al.
6,366,206 B1 4/2002 Ishikawa et al.
6,370,841 B1 4/2002 Chudy et al.
6,438,451 B1 8/2002 Lion
6,464,506 B1 10/2002 Welles
6,471,087 B1 10/2002 Shusterman
6,471,089 B2 10/2002 Liff et al.
6,505,193 B1 1/2003 Musgrave et al.
6,513,679 B2 2/2003 Greenwald et al.
6,529,801 B1 3/2003 Rosenblum
6,597,969 B2 7/2003 Greenwald et al.
6,604,019 B2 8/2003 Ahlin et al.
6,612,890 B1 * 9/2003 Radloff ..... 445/24
6,640,212 B1 10/2003 Rosse
6,670,885 B2 12/2003 Kosaka
6,697,704 B2 2/2004 Rosenblum
6,766,218 B2 7/2004 Rosenblum
6,776,304 B2 8/2004 Liff et al.
6,785,589 B2 8/2004 Eggenberger et al.
6,892,941 B2 5/2005 Rosenblum
7,151,982 B2 12/2006 Liff et al.
7,155,306 B2 12/2006 Haitin et al.
7,251,610 B2 7/2007 Alban et al.
7,254,555 B2 8/2007 Field
7,467,093 B1 12/2008 Newton et al.
7,698,019 B2 4/2010 Moncrief et al.
2001/0025208 A1 9/2001 Bartur
2002/0032582 A1 3/2002 Feeney, Jr. et al.
2002/0062175 A1 5/2002 Lion
2002/0133460 A1 9/2002 Field
2002/0143434 A1 10/2002 Greeven et al.
2002/0165641 A1 11/2002 Manalang et al.
2002/0198624 A1 12/2002 Greenwald et al.
2003/0018496 A1 1/2003 Hambright et al.
2003/0050731 A1 3/2003 Rosemblum
2003/0055531 A1 3/2003 Liff et al.
2003/0060926 A1 3/2003 Yuyama et al.
2003/0088332 A1 5/2003 Rosenblum
2003/0093181 A1 5/2003 Rosenblum
2003/0105554 A1 6/2003 Eggenberger et al.
2003/0105555 A1 6/2003 Lunak et al.
2003/0120384 A1 6/2003 Haitin et al.
2003/0140928 A1 7/2003 Bui et al.
2003/0141981 A1 7/2003 Bui et al.
2003/0149594 A1 8/2003 Beazley
2003/0172002 A1 9/2003 Spira et al.
2003/0191669 A1 10/2003 Fitzgerald et al.
2003/0204415 A1 10/2003 Knowlton
2004/0019464 A1 1/2004 Martucci et al.
2004/0121767 A1 6/2004 Simpson et al.
2004/0148054 A1 7/2004 Schwartz
2004/0172289 A1 9/2004 Kozic
2004/0172301 A1 9/2004 Mihai et al.
2004/0176873 A1 9/2004 Kim
2005/0065645 A1 3/2005 Liff et al.
2005/0080651 A1 4/2005 Morrison et al.
2005/0096785 A1 5/2005 Moncrief et al.
2007/0250210 A1 10/2007 Moncrief et al.
2010/0198615 A1 8/2010 Moncrief et al.
2010/0287007 A1 11/2010 Moncrief et al.

OTHER PUBLICATIONS

Examiner Search Report EIC 3600 for U.S. Appl. No. 11/818,416 dated Mar. 16, 2012, 38 pages.

Canadian Office Action from co-pending application Serial No. 2,544,616 dated Dec. 9, 2011.

Complaint, Case No. 2:10-cv-00363 styled *Tech Pharmacy Services, Inc. d/b/a Advanced Pharmacy and Advanced Pharmacy Services* v. *Provider Meds, LP, Provider Technologies, Inc., ProviderRX of PA, LLC, ProviderRX of Waco, LLC, ProviderRX of Grapevine, LLC, ProviderRX of San Antonio, LLC, ProviderRX of Midland, LLC, Provider Business Solutions, Inc., Pharmacy Technologies, Inc., Pharmacy Solutions, L.P., W PA OnsiteRX and Reef R. Gillum,* in the United States District of Texas Tyler Division, submitted Jul. 22, 2010.

Declaration of James J. Martin and Exhibits, U.S. Appl. No. 10/944,993, submitted on Aug. 23, 2009, 146 pages.

Declaration of James J. Martin and Exhibits, U.S. Appl. No. 11/818,416, submitted on Aug. 23, 2009, 156 pages.

Declaration of James J. Martin and Exhibits, U.S. Appl. No. 11/951,050, submitted on Aug. 23, 2009, 147 pages.

Declaration of James W. Moncrief and Exhibits, U.S. Appl. No. 11/818,416, submitted on Aug. 23, 2009, 156 pages.

Declaration of James J. Moncreif and Exhibits, U.S. Appl. No. 11/951,050, submitted on Aug. 23, 2009, 147 pages.

"Envoy Automated Medication System—Good Medicine Made Simple," by KVM Technologies, Inc., Jan. 14, 1999,18 pgs.

"Envoy Automated Medication System—Managing Your Envoy Pharmacy," 39 pgs.

Erickson, Greg, Unit-of-Use Packaging: The Wave of the Future?, Pharmaceutical & Medical Packaging News, Jun. 1998, pp. 23-26, A Canon Communications LLC Publication.

Forcinio, Hallie. Pharmaceutical Technology North America, "What does pharmacy automation mean for packaging?", Jan. 2002, vol. 26, Iss. 1, p. 22.

"Industry Watch: New Internet-Based System from RNA," ComputerTalk The Magazine for Contemporary Pharmacy Management, May/Jun. 1999, pp. 6-9 & 33, vol. 19, No. 3.

Kokot, Ron, McKee, John, and Stone, David, "Envoy Automated Medication System—Carrington Health System," Dec. 7, 2000, Columbus, OH, 13 pgs.

Pyxis Envoy, Automated Point-Of-Use Packaging and Dispensing System, http://www.pyxis.com/products/altenvoy.asp, Sep. 8, 2004, 1 page.

"RNA Health Information Systems: Your Key to Efficient Healthcare Delivery in a Managed-Healthcare Era," ComputerTalk the Magazine for Contemporary Pharmacy Management, Mar./Apr. 2000, p. 55, vol. 20, No. 2.

Schoettmer, Gary J., R.Ph., "Web Goes Prime Time in Long-Term Care," ComputerTalk The Magazine for Contemporary Pharmacy Management, Sep./Oct. 1999, pp. 24-25, vol. 19, No. 5.
Ukens, Carol, "System Links Nursing Home and Pharmacy to Reduce Drug Errors," Drug Topics The News Magazine for Pharmacists, Aug. 16, 1999.
Office Action for U.S. Appl. No. 11/818,416 dated Mar. 6, 2009, 12 pages.
Response to Office Action dated May 1, 2009, for co-pending U.S. Appl. No. 11/818,416, submitted on Aug. 23, 2009, 14 pages.
Notice of Allowance for U.S. Appl. No. 11/951,050 dated Nov. 23, 2009, 29 pages.
Notice of Allowance for U.S. Appl. No. 11/951,050 dated Jan. 28, 2010, 12 pages.
Office Action for Co-Pending U.S. Appl. No. 11/951,050 dated May 1, 2009, 24 pages.
Supplemental Response to Office Action dated May 1, 2009 for co-pending U.S. Appl. No. 11/951,050, submitted on Aug. 23, 2009, 11 pages.
Response to Office Action dated May 1, 2009, for co-pending U.S. Appl. No. 11/951,050, submitted on Aug. 3, 2009, 12 pages.
Notice of Allowance for U.S. Appl. No. 12/756,285 dated Mar. 2, 2012, 13 pages.
Notice of Allowance for U.S. Appl. No. 12/825,595 dated Mar. 22, 2012, 12 pages.
Buckley, Bruce, Expanding line of Pyxis Products increases productivity, minimizes error, Drug Store News, Nov. 2003, p. 32, A Lebhar-Friedman Publication, New York, NY.
Office Action for U.S. Appl. No. 11/818,416 dated Dec. 9, 2009, 12 pages.
Final Office Action for U.S. Appl. No. 11/818,416 dated Aug. 20, 2010, 14 pages.
Notice of Allowance for U.S. Appl. No. 10/944,993 dated Feb. 26, 210, 7 pages.
Office Action for U.S. Appl. No. 10/944,993 dated Dec. 18, 2008, 15 pages.
Final Office Action for U.S. Appl. No. 10/944,993 dated Jun. 27, 2008, 24 pages.
Office Action for U.S. Appl. No. 10/944,993 dated Aug. 9, 2007, 17 pages.
Office Action for U.S. Appl. No. 10/944,993 dated Aug. 1, 2006, 27 pages.
Final Office Action for U.S. Appl. No. 10/944,993 dated Jul. 10, 2009, 17 pages.
Weber, David O. and Weber, Alexandra L. The Healthcare Forum Journal, "Reshaping the American Hospital", Sep./Oct. 1994, vol. 37, Iss. 5, p. SS1.*
Web page article titled Device Could Ease Pill-Taking Troubles, found at www.jsonline.com dated Jul. 19, 2004.
Pyxis Envoy Automated Point-of-Use Packaging and Dispensing System, found at www.pyxis.com/products/altenvoy.asp dated Sep. 18, 2004.
U.S. Appl. No. 10/944,993, filed Sep. 20, 2004, including arguments from the Examiner and arguments in support of patentability.
U.S. Appl. No. 11/818,418, filed Jun. 14, 2007.
Office Action dated Jul. 10, 2009 for copending U.S. Appl. No. 10/944,993.
Declaration of James W. Moncreif and Exhibits, U.S. Appl. No. 10/944,993, submitted on Aug. 23, 2009, 146 pages.
Declaration of James W. Moncreif and Exhibits, U.S. Appl. No. 11/818,416, submitted on Aug. 23, 2009, 146 pages.
Declaration of James J. Martin and Exhibits, U.S. Appl. No. 11/818,416, submitted on Aug. 23, 2009, 146 pages.
Declaration of James W. Moncreif and Exhibits, U.S. Appl. No. 11/915,050, submitted on Aug. 23, 2009, 147 pages.
Response to Office Action dated May 1, 2009 for co-pending U.S. Appl. No. 11/951,050, submitted on Aug. 23, 2009, 11 pages.
Response to Office Action dated May 1, 2009 for co-pending U.S. Appl. No. 11/951,050, submitted on Aug. 3, 2009, 12 pages.
Response to Office Action dated May 1, 2009 for co-pending U.S. Appl. No. 11/818,416, submitted on Aug. 23, 2009, 14 pages.
Declaration of James W. Moncrief and James J. Martin—Apr. 27, 2009.
Envoy Automated Medication System; Managing Your Envoy Pharmacy, Aug. 8, 2000, 39 pages.
Declaration of James W. Moncrief and James J. Martin—Nov. 8, 2004.
Office Action for Co-pending U.S. Appl. No. 11/818,416 dated Mar. 6, 2009, 12 pages.
Office Action for Co-pending U.S. Appl. No. 10/951,050 dated May 1, 2009, 24 pages.
Manning, Joe, Device could ease pill-taking troubles, JSOnline, Milwaukee Journal Sentinel, http://www.jsonline.com/story/index.aspx?id=238182, Dec. 5, 2007, 4 pages.
Office Action for Co-pending U.S. Appl. No. 11/818,416, dated Dec. 9, 2009, 20 pages.

* cited by examiner

SYSTEM AND SOFTWARE OF ENHANCED PHARMACEUTICAL OPERATIONS IN LONG-TERM CARE FACILITIES AND RELATED METHODS

Matter enclosed in heavy brackets [ ] appears in the original patent but forms no part of this reissue specification; matter printed in italics indicates the additions made by reissue.

RELATED APPLICATIONS

This application is a continuation of and claims the benefit of and priority to U.S. patent application Ser. No. 10/944,993, filed Sep. 20, 2004, titled "System and Software of Enhanced Pharmaceutical Operations in Long-Term Care Facilities and Related Methods," which claims the benefit of and priority to U.S. Provisional Patent Application Ser. No. 60/516,678, filed on Nov. 3, 2003, titled "System and Software of Enhanced Pharmaceutical Operations in Long-Term Care Facilities and Related Methods," each incorporated herein by reference in its entirety.

BACKGROUND OF THE INVENTION

1. Field of the Invention

This invention relates to the nursing home, retirement home, assisted living facility, and other long-term care industries in general and, more particularly, to pharmaceutical operations within nursing homes, retirement homes, assisted living facilities, and other patient care facilities.

2. Description of Related Art

Over the years, pharmacies have been a backbone in providing prescription drugs and other medications to people and have been a convenience as retail pharmacies have expanded to locating close to most residential areas in our country. Recently, pharmacies also have been placed inside of facilities such as hospitals, physician offices, malls, nursing homes, retirement homes, assisted living facilities, and other locations to make it easier for people to get access to medications and to facilitate interaction with medical personnel. Because of the numerous types of medications stored and dispensed by pharmacies, automation within the pharmacy industry has been desirable. Accordingly, numerous developments have been made to automate the pharmacy ordering, dispensing, and storage capabilities. For example, machines have been developed to store and dispense medication responsive to security codes or other identification from medical personnel or users. Also, electronic storage and dispensing carts have been developed which are often stored on each floor of a hospital to allow the carts to electronically receive dispensing instructions from a hospital pharmacy computer. Additionally, machines have been developed to store several hundred different types of medications and to dispense the medications to medical personnel for distribution to patients.

Nevertheless, little has been done to enhance storage and distribution of medications in nursing homes, retirement homes, Alzheimer's living facilities, senior communities, assisted living facilities, and other types of long term care facilities (hereinafter collectively "long-term care facilities") which are significantly different in operation, personnel structure, and physical structure than hospitals, physician offices, and home care. This is increasingly important as the baby boom generation ages and more and more people enter these long-term care facilities. Also, because more and more people are and will be entering these long-term care facilities and because medication costs have been rising over the years, attempting to help male pharmacies, providing services to these long term facilities, profitable can often be important in successfully operating a long-term care facility. Further, error can arise when dispensing medication, and a need still exists to reduce the risk of error in dispensing medication, especially in long-term care facilities.

SUMMARY OF THE INVENTION

In view of the foregoing, embodiments of the present invention advantageously provide a system, software and methods for enhancing pharmaceutical operations in nursing homes, assisted living facilities, retirement homes, and other long-term care facilities. Embodiments of the present invention also advantageously provide a system, software, and methods for enhanced pharmaceutical operations in long-term care facilities that substantially reduces medication shortages, reduces medication preparation time, reduces medication passing or dispensing time, reduces medication waste, enhances documentation, and enhances regulatory acceptance. Embodiments of the present invention additionally provide a system, software, and methods for enhanced pharmaceutical operations in long-term care facilities, which substantially reduce the risk of error associated with dispensing medications to patients in the homes or facilities. Embodiments of the present invention further provide a system, software, and methods for enhanced pharmaceutical operations in long-term care facilities, which enhance profitability of pharmacy business associated with the homes or facilities. Embodiments of the present invention still further provide a system, software, and methods for enhanced pharmaceutical operations, which streamline the medication dispensing procedures for medical personnel working with the long-term care facilities to help make the procedures more efficient and easier.

More particularly, embodiments of the present invention provide a system of enhanced pharmaceutical operation services for long-term care facilities. For example, in an embodiment of the present invention, a system includes a first data processing and management computer including a first memory to store data therein to thereby define a long-term care facility pharmacy group management server. Long-term care facility pharmacy management software stored in the first memory of the long-term care facility pharmacy group management server manages pharmaceutical operations in long-term care facilities. A plurality of pharmaceutical storage and electronic dispensing carts are each positioned in a separate long-term care facility remote from the long-term care facility pharmacy group management server and are in communication with the long-term care facility pharmacy group management server though a communication network to store pharmaceuticals therein and to dispense the pharmaceuticals to authorized healthcare personnel located at the long-term care facility. A second remote pharmacy group computer is positioned remote from and in communication with the long-term care facility pharmacy group management server, and is positioned remote from and in communication with the plurality of pharmaceutical storage and electronic dispensing carts. The second remote pharmacy group computer includes a second memory to store data therein to define a remote pharmacy group server. A plurality of pharmaceutical prescription document processors are each positioned in the long-term care facility where at least one of the plurality of pharmaceutical storage and electronic dispensing carts is located and are in communication with the remote pharmacy group server or the pharmacy group management server to process a pharmaceutical prescription order from the long-term care facility to be delivered to the long-term care facility for storage and dispensing through the at least one of the plurality of pharmaceutical storage and electronic dispensing carts. The system can also include a plurality of video input devices each separately positioned adjacent a respective one of the plurality of pharmaceutical storage and electronic dispensing carts remote from and in communication with at least one of the long-term care facility pharmacy group management server and the remote pharmacy group server. Each video input device is positionable to produce a video image of facility health care personnel and preferably is positionable to view visually accessible functional components of the adjacent pharmaceutical storage and electronic dispensing cart. This allows for the provision of visual feedback to pharmacy personnel to allow for enhanced training facility health-care personnel and for troubleshooting the pharmaceutical storage and electronic dispensing cart. The system also can include a pharmaceutical storage facility associated with the remote pharmacy group server and having a plurality of pharmaceuticals stored therein. The pharmaceutical storage facility has at least one vehicle to facilitate delivery of the pharmaceuticals at the storage facility to each of the plurality of pharmaceutical storage and electronic dispensing carts at the plurality of long-term care facilities responsive to the pharmaceutical prescription order.

According to an embodiment of the present invention, a system of enhanced pharmaceutical operation services for long-term care facilities can include a pharmacy group management computer defining a long-term care facility pharmacy group management server, and long-term care facility pharmacy management software associated with the long-term care facility pharmacy group management server to manage pharmaceutical operations in a plurality of long-term care facilities. A plurality of pharmaceutical storage and electronic dispensing carts are each positioned in a long-term care facility separate and remote from the long-term care facility pharmacy group management server to store pharmaceuticals therein and to dispense the pharmaceuticals to authorized health care personnel located at the long-term care facility. The plurality of pharmaceutical storage and electronic dispensing carts and a plurality of pharmaceutical prescription document processors are each positioned in a long-term care facility remote separate from and in communication with the long-term care facility pharmacy group management server or a remote pharmacy group computer or server to process a pharmaceutical prescription order from the long-term care facility and to be delivered to the long-term care facility.

Additionally, according to an embodiment of the present invention, a system of enhanced pharmaceutical operation services for long-term care facilities can include a first pharmacy group management computer defining a long-term care facility pharmacy group management server and long-term care facility pharmacy management software associated with the long-term care facility pharmacy group management server to manage pharmaceutical operations in a plurality of long-term care facilities. A plurality of pharmaceutical storage and electronic dispensing carts are each positioned in each one of the plurality of long-term care facilities remote from the long-term care facility pharmacy group management server and in communication with the long-term care facility pharmacy group management server to store a plurality of different pharmaceuticals, package a plurality of individual doses of pharmaceuticals, and dispense the plurality of individual doses of pharmaceuticals to authorized facility medical personnel located at one of the plurality of long-term care facilities. A remote pharmaceutical dispensing and storage facility is positioned remote from the plurality of pharmaceutical storage and electronic dispensing carts and is associated with a second remote pharmacy group computer defining a remote pharmacy group server which is also in communication with the long-term care facility pharmacy group management server and each of the plurality of pharmaceutical storage and electronic dispensing carts through the communication network. The remote pharmaceutical dispensing storage facility has a plurality of pharmaceuticals stored therein and has at least one vehicle positioned to deliver selected pharmaceuticals at the storage facility to each of the plurality of pharmaceutical storage and electronic dispensing carts. Delivery, preferably along a preplanned or preselected delivery route, is accomplished in response to a combination of individual facility patient pharmaceutical dispensing instructions and medication inventory for each of the plurality of pharmaceutical storage and electronic dispensing carts.

Embodiments of the present invention provide long-term care facility pharmacy management software adapted to be stored on the storage media. For example, in an embodiment of the present invention, the software includes a patient prescription receiver which receives a digital image of a patient medication prescription order from a pharmaceutical prescription document processor associated with a remote medication dispensing apparatus, such as the above described pharmaceutical storage and dispensing device, to store the digital image of the patient medication prescription and to queue the digital image for prescription order processing. A queue receives the digital image and holds the digital image for a prescription order requirements entry and release verification by a remote pharmacy pharmacist. A drug conflict analyzer, responsive to the prescription order requirements and data contained within the patient record, can analyze the prescription order requirements against a patient medication profile, a patient allergy profile, a patient diagnosis profile, a patient insurance profile, and a drug interaction profile, to determine if a conflict exists. If no conflict is found, a dispensing initiator positioned to receive the medication inventory for each of the pharmaceutical storage and electronic dispensing carts and responsive to the release verification performed by the remote pharmacy pharmacist, can transmit individual facility patient pharmaceutical dispensing instructions to the respective pharmaceutical storage and electronic dispensing cart over the communication network to thereby initiate patient medication dispensing.

According to an embodiment of the present invention, the pharmacy management software is adapted to be stored on a storage media associated with a pharmacy group management computer to manage pharmaceutical operations in a remote pharmaceutical dispensing and storage facility and a plurality of remotely positioned, e.g., long-term patient care facilities each having a medication dispensing apparatus. The software is further adapted to accept prescriptions from a physician, patient identification information and pharmaceutical inventory from the medication dispensing apparatus, and insurance information from the patient's insurance company. This allows the software to control dispensing medication from the medication dispensing apparatus to an authorized health-care personnel in each of the long-term care facilities, to control inventory in the medication dispensing apparatus, to order delivery of pharmaceuticals from the remote pharmaceutical dispensing and storage facility to restock the medication dispensing apparatus or for individually tailored prescription delivery for those prescriptions not stocked in the medication dispensing apparatus, and to electronically process medication claims with a reimbursement provider.

Embodiments of the present invention also provide pharmacy management software stored on a storage media associated with a pharmacy group management computer for managing pharmaceutical operations in a remote pharmacy and a plurality of remotely positioned, e.g., long-term patient care facilities each having at least one remote medication dispensing apparatus. According to an embodiment of the pharmacy management software, the pharmacy management software can include a set of instructions that when executed by a computer, cause the computer to perform the operations of providing instructions to each of a plurality of pharmaceutical storage and electronic dispensing carts or other medication dispensing apparatus for dispensing medication to a plurality of, e.g. long-term care, patients at the plurality of, e.g. long-term care patient facilities according to patient specific prescription requirements, receiving dispensing data from each of the plurality of pharmaceutical storage and electronic dispensing carts, providing separate billing records including billing data, indexed by reimbursement provider, for each of the plurality of patients at each of the plurality of long-term care facilities, and consolidating billing data including billing data for medications dispensed to a respective patient from at least one of the plurality of pharmaceutical storage and electronic dispensing carts and billing data for medications not dispensed from at least one of the plurality of pharmaceutical storage and electronic dispensing carts. The operation of consolidating billing data can include consolidating billing data by patient, consolidating billing data by long-term care facility, consolidating billing data by remote pharmacy, and/or consolidating billing data by reimbursement provider. The operations can also include submitting separate consolidated reimbursement claims electronically to each respective reimbursement provider.

According to an embodiment of the pharmacy management software, the pharmacy management software can include a set of instructions that when executed by the computer, cause the computer to perform the operations of providing separate billing records for each of a plurality of patients at a patient care facility, consolidating billing data by reimbursement provider to thereby generate reimbursements from one or more reimbursement providers, and submitting separate consolidated reimbursement claims to each respective reimbursement provider. The billing data can include billing data for medications dispensed to a respective patient from at least one of the pharmaceutical storage and electronic dispensing carts. The billing data can further include billing data for medications not dispensed from at least one of the plurality of pharmaceutical storage and electronic dispensing carts, such as, for example, those dispensed the traditional way, e.g., due to an incompatibility with the pharmaceutical storage and electronic dispensing cart, or other reasons known to those skilled in the art. The operations can also include, e.g., electronically submitting consolidated reimbursement claims for each patient to a respective patient representative.

Further, embodiments of the present invention also can include a computer readable medium that is readable by a computer to manage pharmaceutical operations in a remote pharmaceutical dispensing and storage facility defining a remote pharmacy and in a plurality of remotely positioned long-term care facilities each having at least one remote pharmaceutical dispensing and storing apparatus in communication with the computer and having a memory and a plurality of medication dispensing cartridges associated therewith. In an embodiment of the present invention, the computer readable medium includes a set of instructions that, when executed by the computer, cause the computer to perform the operations of establishing remote communications between each pharmaceutical storage and dispensing apparatus and the remote pharmacy, registering at least one patient for each of the plurality of, e.g., long-term patient care facilities in a database of residents for the long-term care facility associated with a pharmaceutical storage and dispensing apparatus located at that long-term care facility, storing in memory of each pharmaceutical storage and dispensing apparatus at least one medication type, an amount of medication to be dispensed, and a medication dispensing time, dispensing medication responsive to patient prescription requirements for each patient registered to the pharmaceutical storage and dispensing apparatus located at each respective long-term care facility, and maintaining a record of medication dispensed and an inventory of medication remaining in each cartridge of each pharmaceutical storage and dispensing apparatus.

According to an embodiment of the present invention, a computer readable medium that is readable by a computer to manage pharmaceutical operations can include instructions that when executed by a computer, cause the computer to perform the operations of: providing separate billing records for each of a plurality of patients at each of a plurality of patient care facilities such as, for example, long-term care facilities; and consolidating billing data by reimbursement provider to thereby generate reimbursements from one or more reimbursement providers. The billing data can include billing data for medications dispensed to a respective patient from at least one of a plurality of pharmaceutical storage and electronic dispensing carts and billing data for medications not dispensed from at least one of the plurality of pharmaceutical storage and electronic dispensing carts, such as, for example, those dispensed the traditional way, e.g., due to incompatibility with the pharmaceutical storage and electronic dispensing cart, or other reasons known to those skilled in the art. The operation of consolidating billing data can include consolidating billing data by patient, consolidating billing data by long-term care facility, consolidating billing data by remote pharmacy, or consolidating billing data by reimbursement provider. The operations can further include submitting, e.g., electronically, the consolidated reimbursement claims for each of the plurality of patients, to one or more reimbursement providers. According to an embodiment of the computer readable medium, the consolidated reimbursement claims can be submitted in a batch form to allow for batch-type processing by a reimbursement provider.

Embodiments of the present invention also include methods of providing pharmaceutical services to long-term care facilities. A method includes providing a pharmacy remote from a plurality of long-term care facilities to define an long-term care facility pharmacy, restructuring long-term care facility staff procedures for communication between long-term care facility staff and the long-term care facility pharmacy, restructuring medication procurement and resident medication distribution procedures within the plurality of long-term care facilities, installing a pharmaceutical storage and electronic dispensing cart at each of the plurality of the long-term care facilities to be used by the long-term care facility staff, and visiting each of the plurality of long-term care facilities on a preselected frequency by pharmacy staff from the remote pharmacy to assess performance and enhance communication.

By restructuring long-term care facility staff communication procedures and medication procurement and patient distribution procedures, embodiments of the present invention advantageously enhance pharmaceutical operations by allowing an individual long-term care facility to participate in a broader network of a plurality of long-term care facilities to thereby participate in costing and delivery benefits of the plurality or group of long-term care facilities. Such group participation streamlines operational procedures and communication and enhances profitability of the individual long-term care facilities.

Embodiments of the present invention also include methods for generating revenue from a plurality of long-term care facilities each devoid of an on-location pharmacy. For example, in an embodiment of the present invention, a method includes reducing management overhead costs and reducing pharmaceutical delivery costs. Management overhead costs can be reduced by assigning each of the plurality of long-term care facilities at least one automated pharmaceutical storage and dispensing cart to reduce workload of facility staff members, assigning a plurality of the long-term care facilities to each of at least one long-term care facility remote pharmacy, and assigning the at least one long-term care facility remote pharmacy to a single long-term care facility pharmacy group manager, to thereby continuously monitor multiple long-term care facilities. Pharmaceutical delivery costs can be reduced by delivering pharmaceuticals by remote pharmacy vehicle to replenish, in a single delivery iteration, each of a plurality of the automated pharmaceutical storage and dispensing carts and to provide those pharmaceuticals according to the patient prescription requirements and not provided by each respective pharmaceutical storage and electronic dispensing cart.

Still further, in an embodiment of the present invention, a method includes providing a pharmacy remote from a plurality of long-term care facilities to define a long-term care facility remote pharmacy, positioning at least one pharmaceutical storage and dispensing apparatus having at least one removable medicine cartridge in each of the plurality of long-term care facilities to store and dispense pharmaceuticals to a patient living therein, and establishing remote communications between each pharmaceutical storage and dispensing apparatus and the remote pharmacy. This results in a generation of revenue due to cost savings for both the pharmacy and the long-term care facilities and secures a stable level of sales. Patients for each of the plurality of long-term care facilities are then registered in a database of residents for the long-term care facility associated with a respective pharmaceutical storage and dispensing apparatus located at that long-term care facility, the database stored in memory of a data processing and management computer. At least one medication type, amount to be dispensed, and a medication dispensing time is then remotely programmed into each pharmaceutical storage and dispensing apparatus, and medication is dispensed according to patient prescription requirements for each associated registered patient. An inventory of medication dispensed and medication remaining can be maintained in the pharmaceutical storage and dispensing apparatus and transmitted directly or indirectly to the remote pharmacy to allow for just-in-time type resupply of the pharmaceutical storage and dispensing apparatus. Further, separate billing records along with consolidated billing data can be supplied for each plurality of registered patients at each of the plurality of long-term care facilities. The methodology allows for the consolidated billing data to be organized by patient, facility, remote pharmacy, and reimbursement provider. This again reduces overhead to the pharmacy and the facility and can allow for batch-type processing by a reimbursement provider.

BRIEF DESCRIPTION OF THE DRAWINGS

So that the manner in which the features and benefits of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

The present invention now will be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Figure 1A:
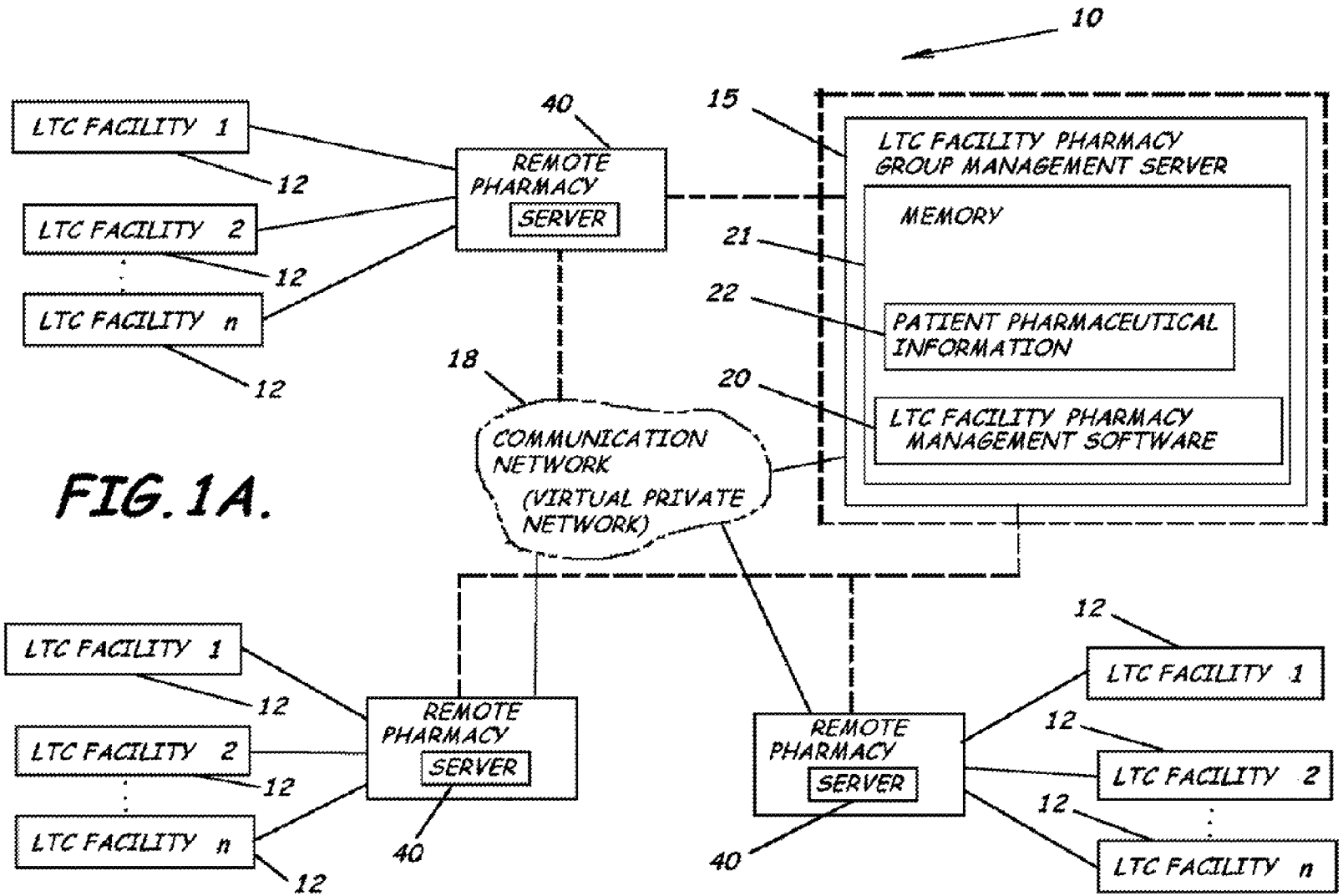
FIG. 1A is a schematic block diagram of a plurality of remote pharmacy group computers networked to a remote pharmacy group management server of a system and software for enhanced pharmaceutical operations in long-term care facilities according to an embodiment of the present invention.
Figure 1B:
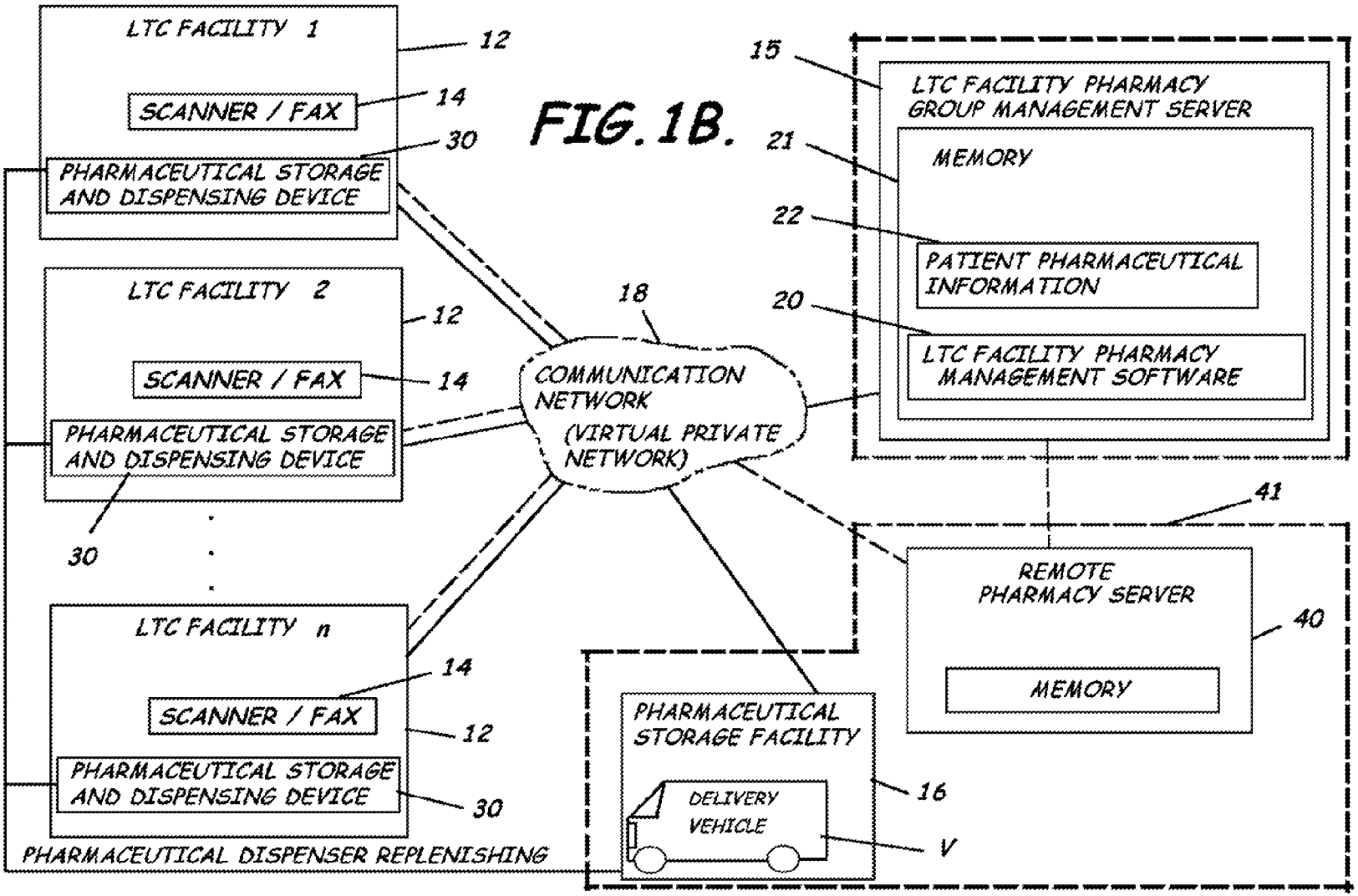
FIG. 1B is a schematic block diagram of a remote pharmacy group computer networked to a plurality of long-term care facilities of a system and software for enhanced pharmaceutical operations in long-term care facilities according to an embodiment of the present invention.
Figure 2:
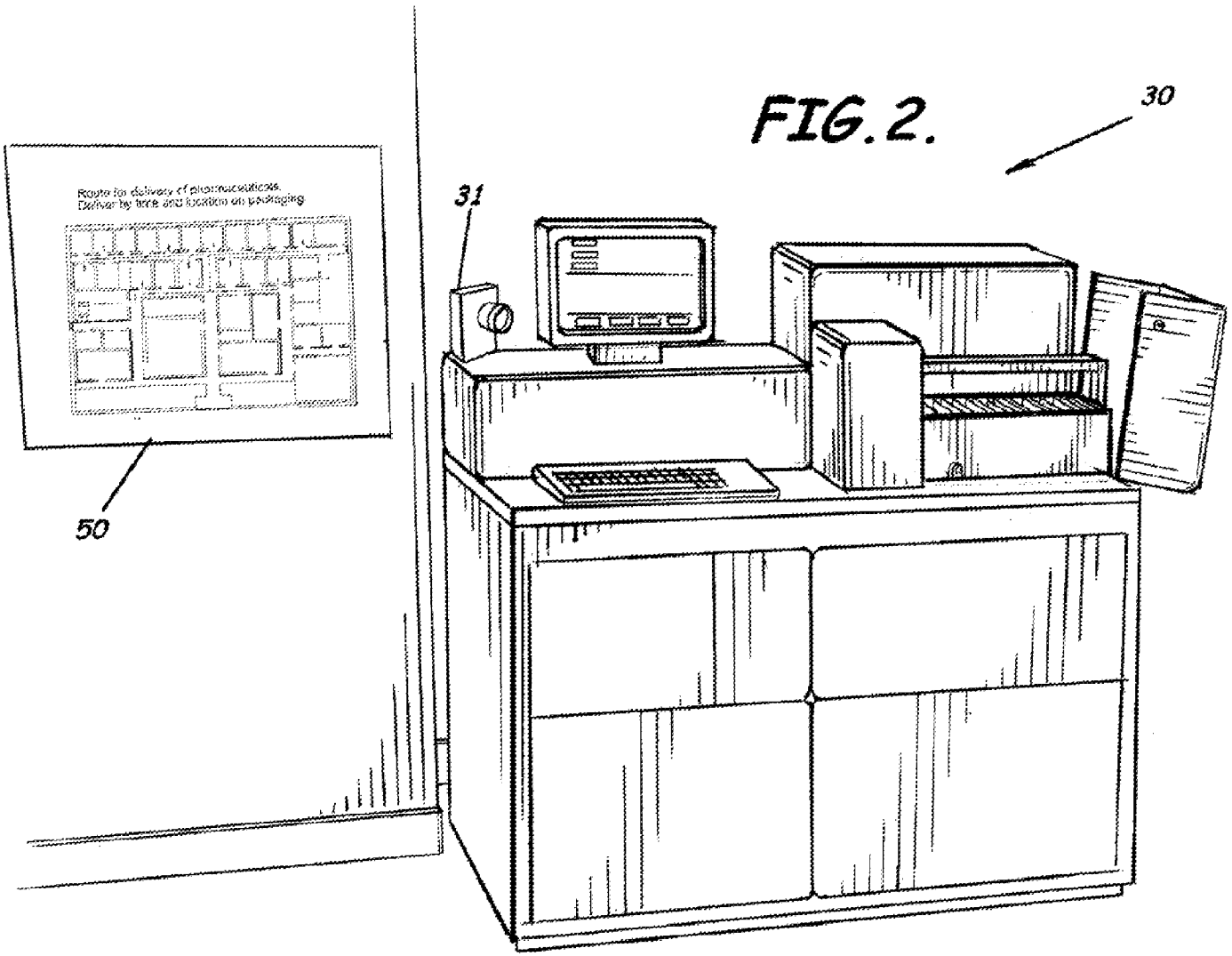
FIG. 2 is an environmental perspective view of a medication storage and dispensing apparatus and a long-term care facility operational diagram of a system, software, and method for enhanced pharmaceutical operations in a long-term care facility according to an embodiment of the present invention.
Figures 3, 4A, 4B:
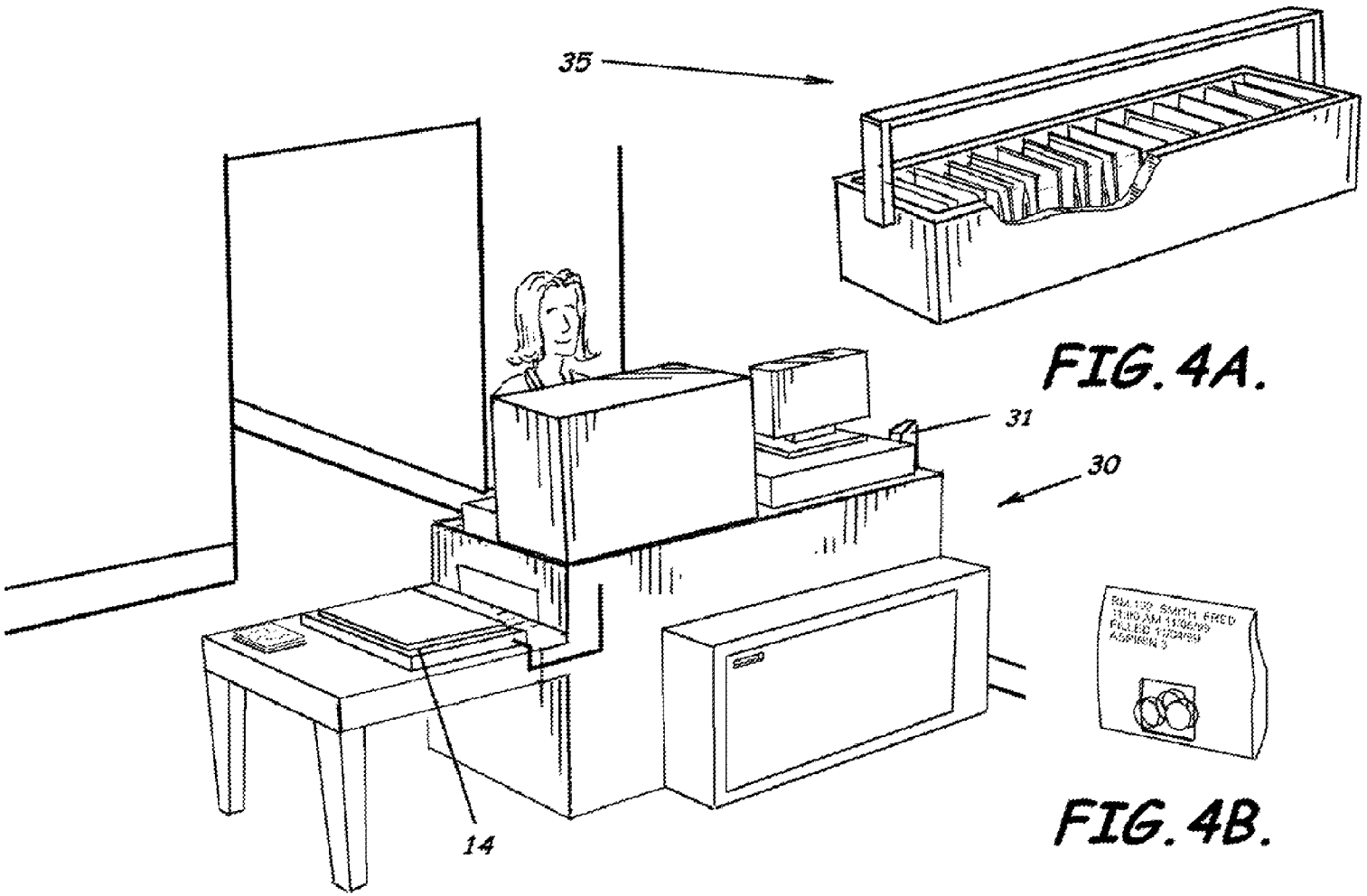
FIG. 3 is an environmental perspective view of medical personnel using a medication storage and dispensing apparatus of a system, software, and method of enhanced pharmaceutical operations in long-term care facilities according to an embodiment of the present invention.
FIG. 4A is a perspective view of a medication dispensing tray/caddie of a medication storage and dispensing apparatus of a system for enhanced pharmaceutical operations according to an embodiment of the present invention.
FIG. 4B is a perspective view of one of the medication dispensing envelopes in the medication dispensing tray/caddie of FIG. 4A according to an embodiment of the present invention.
Figure 9:
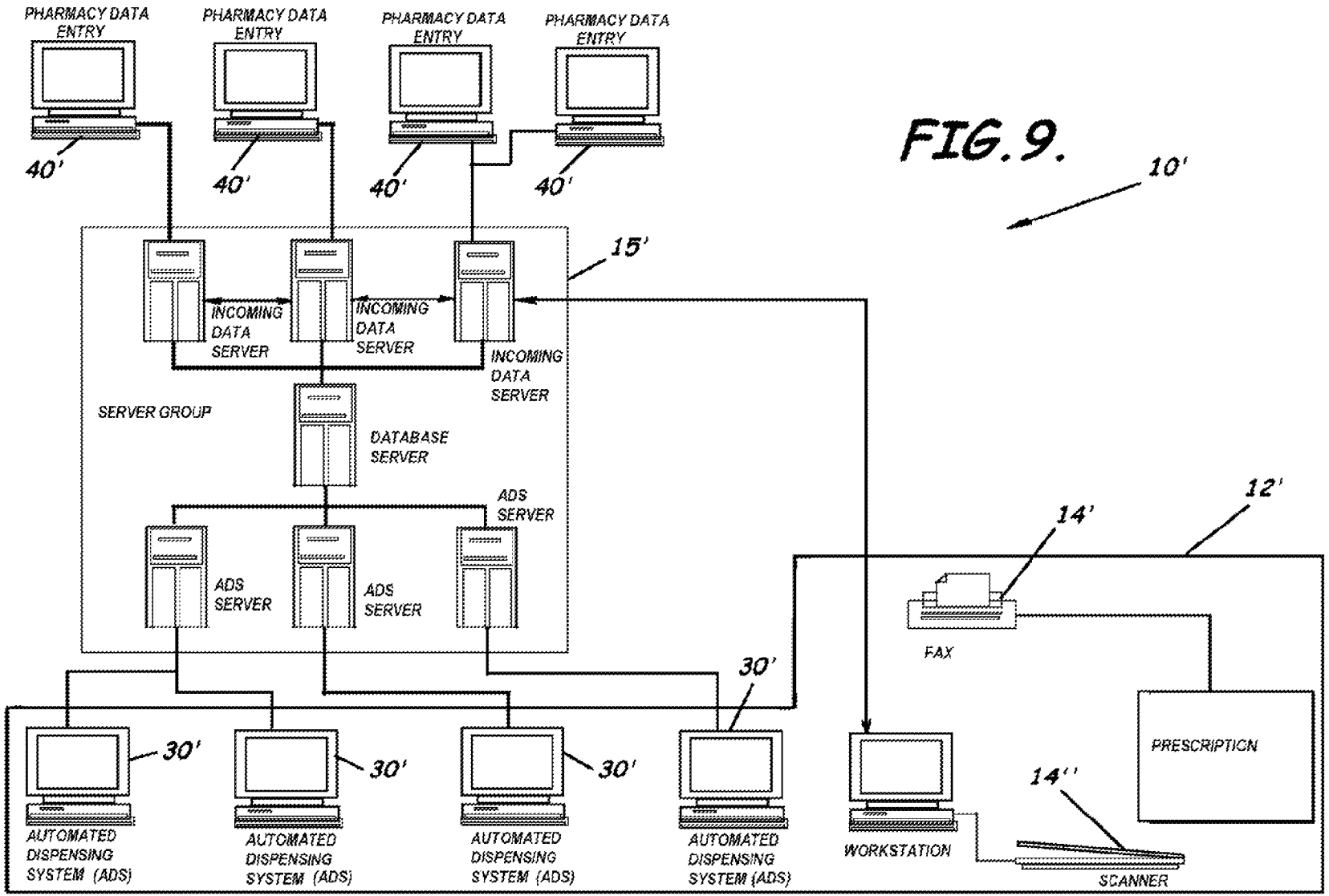
FIG. 9 is a schematic diagram of a system for enhanced pharmaceutical operations in long-term care facilities according to an alternative embodiment of the present invention.

FIGS. 1A-1B illustrate a system 10 of enhanced pharmaceutical operation services for long-term care facilities 12 according to an embodiment of the present invention that includes a data processing and management computer including a memory 21 to store data therein thereby to define a long-term care facility pharmacy group management server 15, long-term care facility pharmacy management software 20 stored in the memory 21 of the long-term care facility pharmacy group management server 15 to manage pharmaceutical operations in long-term care facilities 12, and a communications network 18 in communication with the long-term care facility pharmacy group management server 15. An alternative embodiment of such a system 10' is illustrated in FIG. 9 as well.

As perhaps best shown in FIGS. 2-5, the system 10 also includes a plurality of pharmaceutical storage and electronic dispensing machines or carts 30 each positioned in a separate long-term care facility 12 remote from the long-term care facility pharmacy group management server 15 and in communication with the long-term care facility pharmacy group management server 15 through the communication network 18 to store pharmaceuticals therein and to dispense the pharmaceuticals to authorized health care personnel located at the long-term care facility 12. Each of the plurality of pharmaceutical storage and electronic dispensing machines or carts 30 store a plurality of different pharmaceuticals, e.g., 176 oral solid medications as well as additional bulk storage capabilities, package a plurality of individual doses of pharmaceuticals, dispense the plurality of individual doses of pharmaceuticals to authorized healthcare personnel at the long-term care facilities, and are well understood by those skilled in the art. An example of such a pharmaceutical storage and electronic dispensing machine or cart 30, as understood by those skilled in the art, is the PyxisEnvoy™ by Pyxis Corporation of San Diego, Calif. The PyxisEnvoy, for example, is a dispensing machine capable of securely storing bulk medication for automated patient-specific dispensing. The PyxisEnvoy is capable of packaging medications in individual patient-specific envelopes, both on-demand or at a predetermined time interval, and can organize the patient's envelopes into medication carriers. The envelopes can be further organized whereby "first dose" medications and PRN medications are positioned into separate medication carriers. Further, each envelope can be labeled by the machine with the patient's name, room number, medication, and strength. The PyxisEnvoy can store bulk medications in refill cartridges and containers providing an on-site reserve supply of medications. The PyxisEnvoy, for example, advantageously has the necessary hardware to be remotely controllable from an off-site location and the ability to receive or interface with additional software. As will be understood by those skilled in the art, other types of dispensing carts can be used as well according to the present invention.

Each of the pharmaceutical storage and electronic dispensing machines or carts 30 has associated software which interfaces with and communicates with the pharmacy group management software 20 so that once preselected block times and other system parameters of the embodiments of the present invention are implemented, data entry can be performed by a pharmacy remote from the long-term care facility 12. Also, once preselected block times are established, the pharmaceutical storage and electronic dispensing machines or carts 30 can automatically, i.e. responsive to predetermined commands in memory, package all scheduled medications and perform a regularly scheduled catch-up run to process new or changed medication orders.

As understood by those skilled in the art, these machines or carts 30 package medication in patient specific envelopes sorted in a preselected order, e.g., an order specified by the long-term care facility 12. Advantageously, there is no need to punch medications out of a blister pack into a cup or to search an entire medication cart for a vial of medication, e.g., that someone forgot to reorder. Because these pharmaceutical storage and electronic dispensing machines or carts 30 can store large amounts, e.g., 176, of different medications and can dispense these medications, long-term care facilities 12 do not have to constantly reorder medications. The system 10 and methods maintain an inventory of the number of medications dispensed and number available for dispensing. Each container of the 176 working inventory containers includes a memory chip (not shown), as understood by those skilled in the art, for such inventory control and lot tracking of the medication. Each machine or cart 30 can have a separate removable medicine cartridge (not shown) for each medication type. The system 10 and methods fill these machines or carts 30 at preselected intervals, e.g., once a week, or as needed based on current inventory and usage rate.

As shown in FIGS. 1A and 1B, the system 10 additionally can include a remote pharmacy group computer. The remote pharmacy group computer is positioned remote from the long-term care facility pharmacy group management server 15, in communication with the long-term care facility pharmacy group management server 15 and the plurality of pharmaceutical storage and electronic dispensing carts 30 through the communication network 18, and has a memory to store data therein, to define a remote pharmacy group server 40. The remote pharmacy group server 40 is preferably located in a remote pharmaceutical dispensing and storage facility defining a remote pharmacy 41.

The system 10 can also include a plurality of pharmaceutical prescription document processors 14, e.g., facsimile machines, scanners, or other document processing machines, computers, or equipment as understood by those skilled in the art, each positioned in a long-term care facility 12 remote from and in communication with the remote pharmacy group server 40 to process a pharmaceutical prescription order from the long-term care facility 12 to be delivered to the long-term care facility 12.

Each of a plurality of preferably non-stationary video input devices 31 (FIG. 2), such as a digital, analog, or other type of camera, charge coupled device, digital imaging source, or other device to capture images, as understood by those skilled in the art, can be positioned in one of the long-term care facilities 12 adjacent and preferably interfaced with a respective one of the plurality of pharmaceutical storage and electronic dispensing carts 30 remote from and in communication with at least one of the long-term care facility pharmacy group management server 15 and the remote pharmacy group server 40. The video input devices 31 are positionable to produce for display over the communications network 18 a video image of facility medical personnel and visually accessible functional components of the pharmaceutical storage and electronic dispensing cart 30, including e.g. the prescription document processor 14. This functionality advantageously provides visual feedback to pharmacy personnel to train the facility medical personnel and for troubleshooting the pharmaceutical storage and electronic dispensing cart 30.

The system 10 can also include a pharmaceutical storage facility 16 associated with the remote pharmacy group server 40 and having a plurality of pharmaceuticals stored therein and at least one vehicle V to facilitate delivery of the pharmaceuticals at the storage facility to each of the plurality of pharmaceutical storage and electronic dispensing carts 30 at the plurality of long-term care facilities 12, responsive to the pharmaceutical prescription order.

Figure 7:
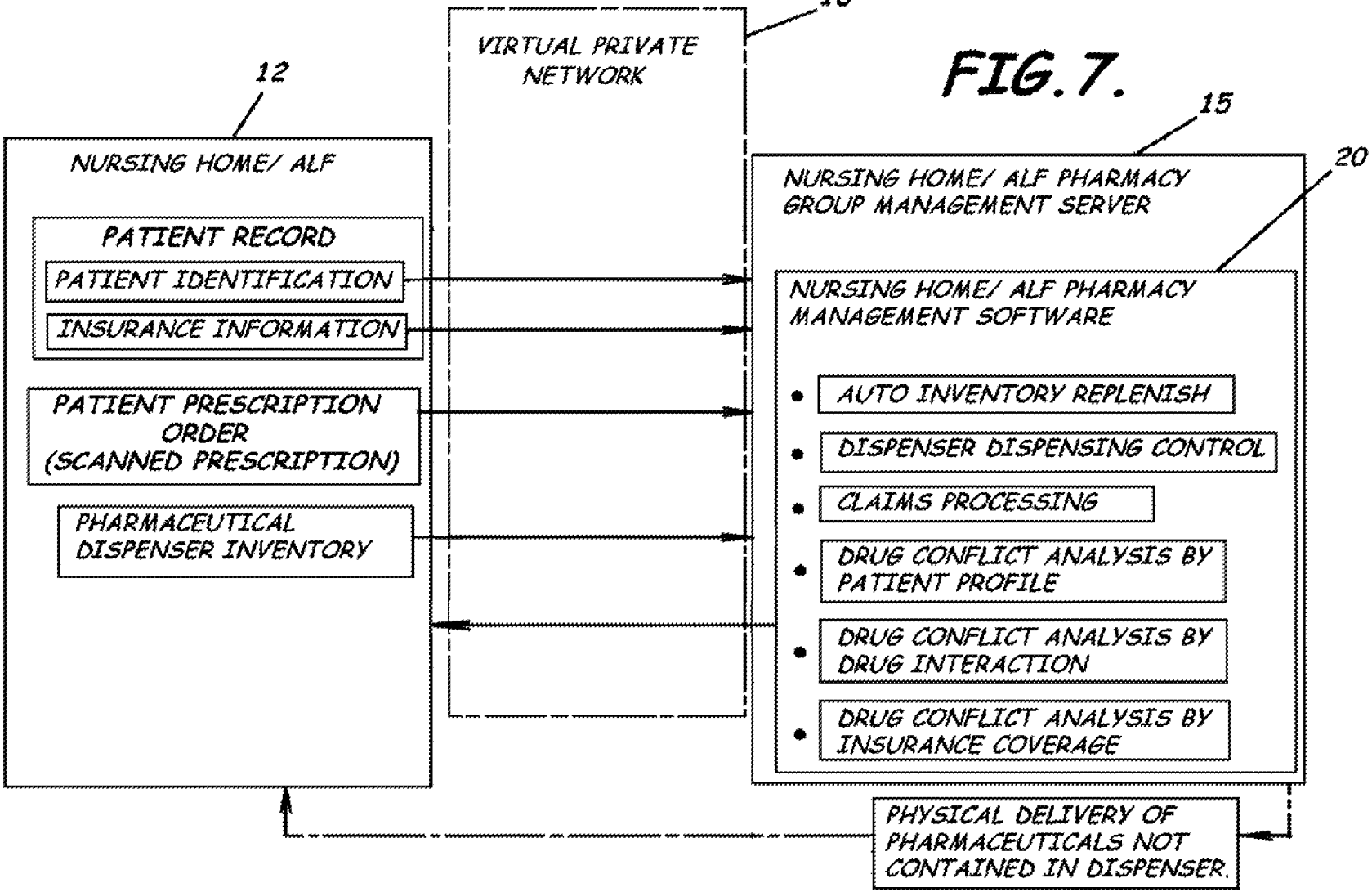
FIG. 7 is a schematic block diagram of a system and software for enhanced pharmaceutical operations of long-term care facilities according to the present invention.
Figure 8A:
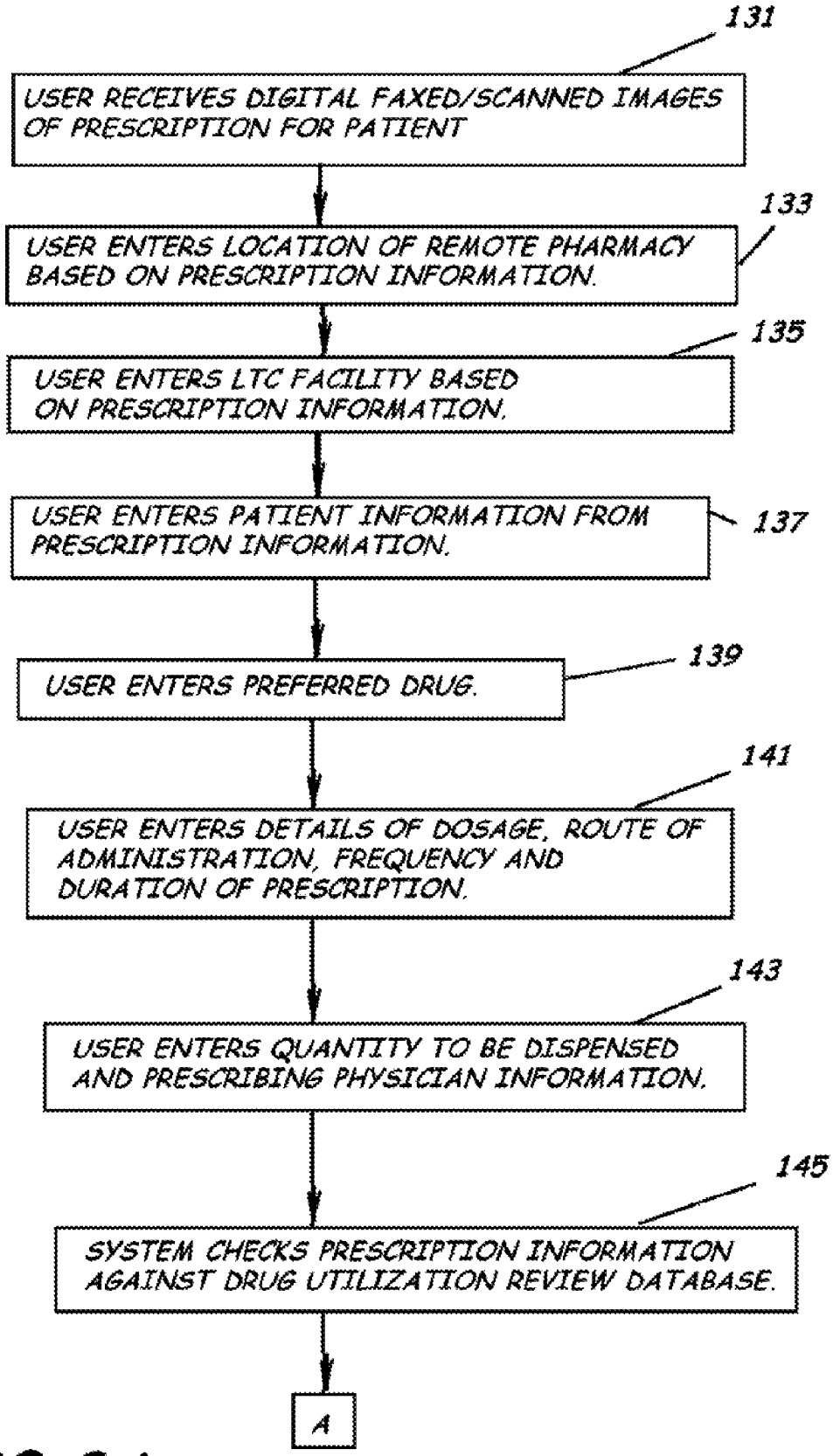
FIG. 8A is a partial schematic flow diagram of software and methods for enhanced pharmaceutical operations in long-term care facilities according to an embodiment of the present invention.
Figure 8B:
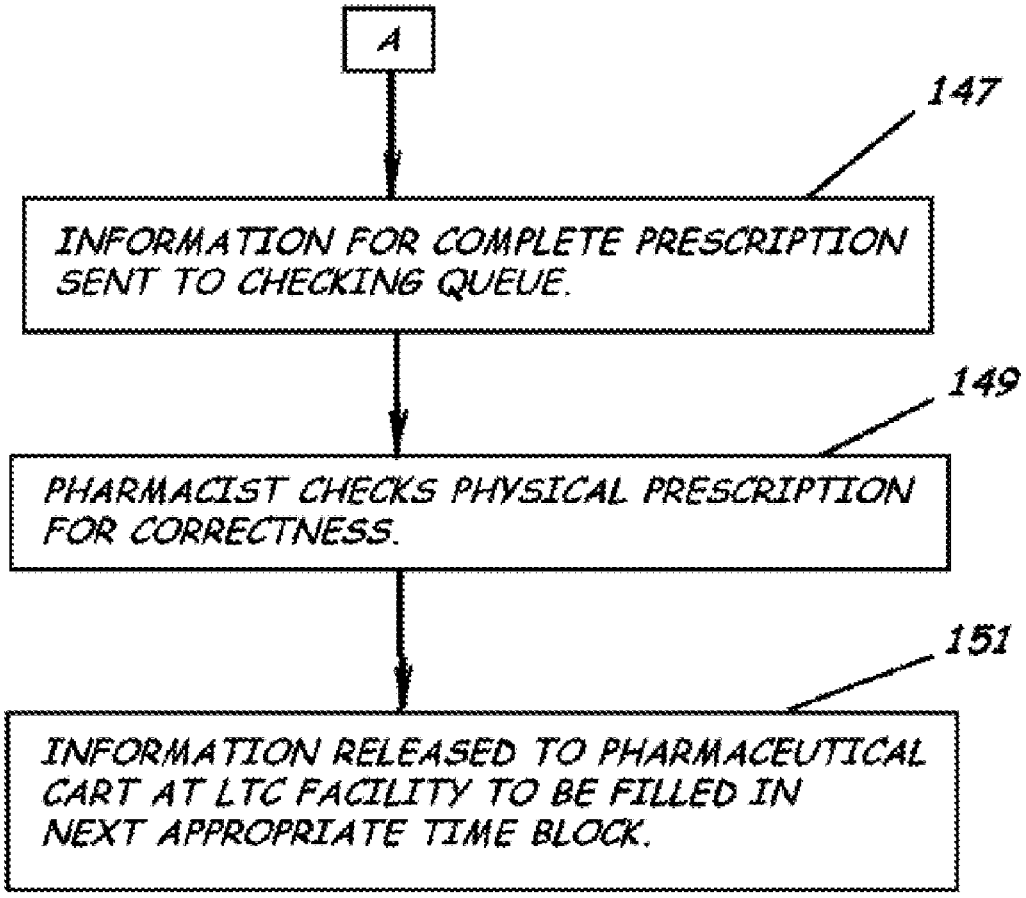
FIG. 8B is a partial schematic flow diagram of software and methods for enhanced pharmaceutical operations in long-term care facilities according to an embodiment of the present invention.
Figure 8C:
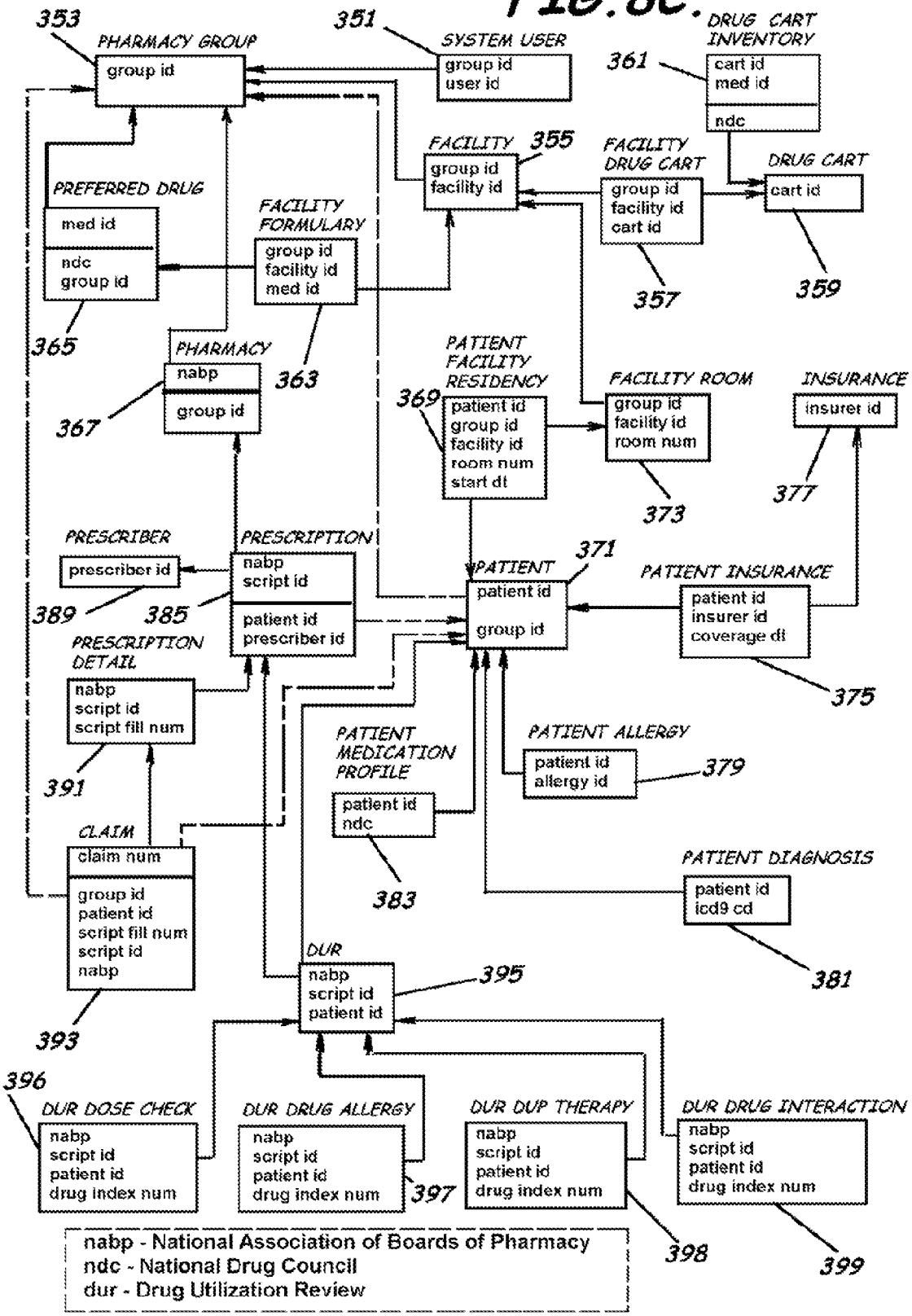
FIG. 8C is a schematic block diagram of database software of a system for enhanced pharmaceutical operations in long-term care facilities according to an embodiment of the present invention.
Figure 10:
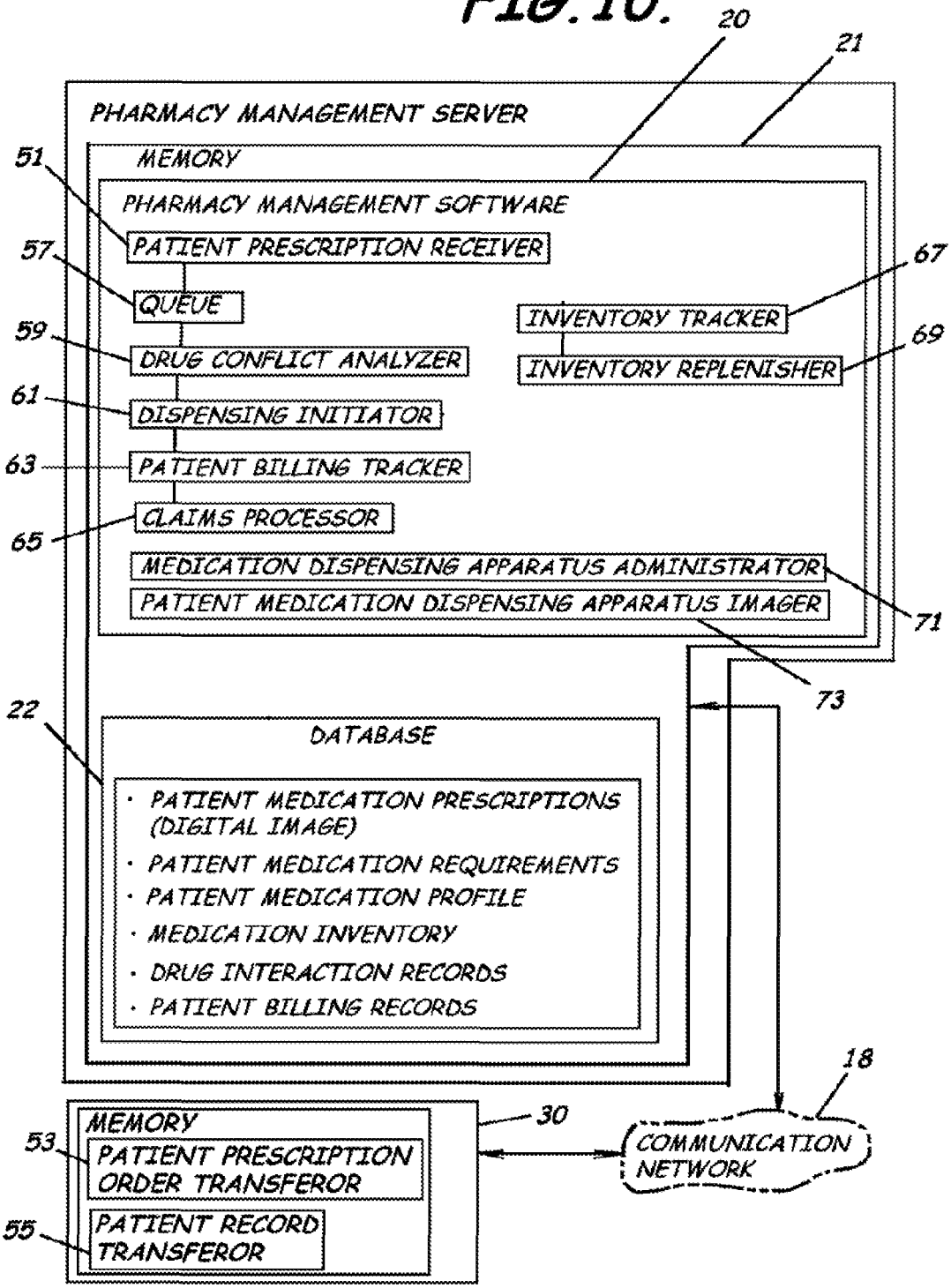
FIG. 10 is a partial schematic diagram of software to enhance pharmaceutical operations in long-term care facilities according to an embodiment of the present invention.
Figure 11:
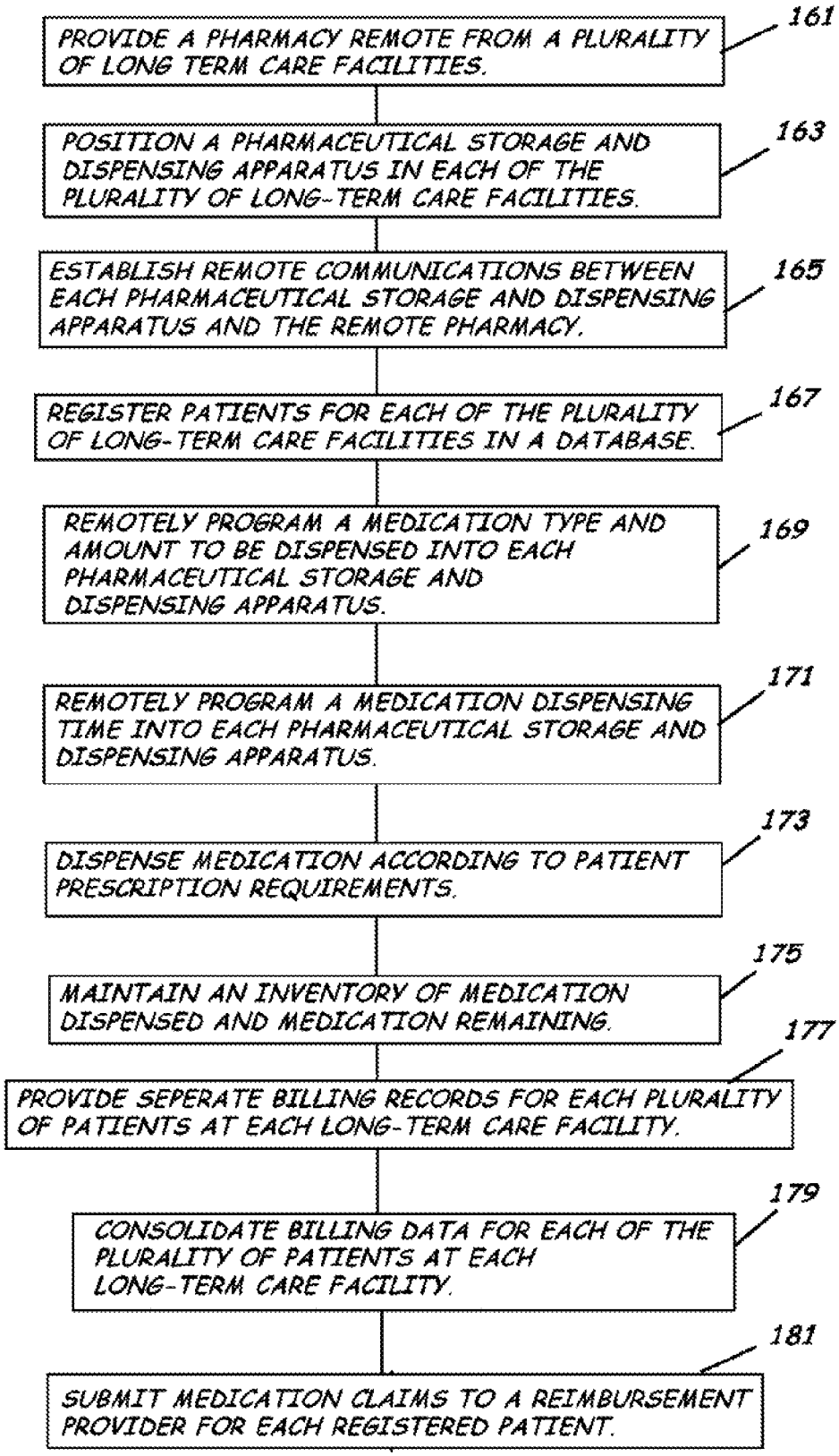
FIG. 11 is a schematic flow diagram of a method of generating revenue from a plurality of long-term care facilities devoid of an on-location pharmacy according to an embodiment of the present invention.

As perhaps best shown in FIGS. 7, 8C, and 10, the long-term care facility pharmacy management software 20 is particularly adapted to accept prescriptions from a physician, patient identification information from the long-term care facility, facility information, insurance information from the patient's insurance company, claim information, drug utilization review, and pharmaceutical inventory from the pharmaceutical storage and dispensing machines or carts 30 (FIG. 2) to control inventory in each of the plurality of pharmaceutical storage and electronic dispensing machines or carts 30 and to order delivery of pharmaceuticals to restock the dispensing carts 30 or for individually tailored prescription delivery by the vehicles V (FIG. 1B) for those prescriptions not stocked in the dispensing carts 30. The long-term care facility pharmacy management software 20, for example, also can include automated inventory replenishment of the dispensing carts 30, dispensing cart dispensing control, claim processing, prescribed drug conflict analysis based on patient medication profile, allergies, diagnosis, prescribed drug conflict analysis based on prescribed drug interaction, and prescribed drug analysis based on patient insurance coverage. Note, the software 20 can be in the form of microcode, programs, routines, and symbolic languages that provide a specific set for sets of ordered operations that control the functioning of the hardware and direct its operation, as known and understood by those skilled in the art.

As shown in FIGS. 1-12C, embodiments of the system 10 include pharmacy management software 20 and methods designed to deliver pharmaceutical operation services to a plurality of long-term care facilities 12, e.g., staff and residents, positioned remotely from a pharmacy and utilizing a plurality of pharmaceutical storage and dispensing carts 30 in the long-term care facility 12, in a manner that significantly enhances the synergistic relationships of healthcare providers involved in the daily care of residents. The system 10 advantageously uses hardware, software, and robotics to converge previously disparate healthcare providers at the resident's side. The financial, social, and medical impact of long-term care facility providers communicating in real-time or near real time with near real-time medication delivery provides significant cost reduction for healthcare payors. It is thought that millions, or even billions, of dollars of medication are wasted each year due to a combination of poor communication between long-term care providers and prior art medication delivery systems.

As shown in FIG. 10, much of the above identified software 20 can be implemented utilizing various components or modules. Note, though shown positioned together, various parts of the software 20, once loaded via a computer readable medium, can be functionally distributed at various locations within the system 10.

In an embodiment of the present invention, the software 20 includes a patient prescription receiver 51 which receives a digital image of a patient medication prescription order from a pharmaceutical prescription document processor 14 associated with a remote medication dispensing apparatus, such as pharmaceutical storage and dispensing device 30, to store the digital image of the patient medication prescription and to queue the digital image for prescription order processing. A patient prescription order transferor 53, preferably stored in memory of the pharmaceutical storage and dispensing device 30 transmits over the communication network 18 the digitized image of the patient medication prescription order received from an associated pharmaceutical prescription processor 14 to the pharmacy group management server 15 or remote pharmacy group server 40, in response to a release initiated by either a pharmacy staff member or a facility staff member. This provides the pharmacy group management server 15 or remote pharmacy group server 40 with patient medication requirements which can be stored in database 22. Correspondingly, a patient record transferor 55 also preferably stored in the memory of the pharmaceutical storage and dispensing device 30 can transmit either a patient record or select portions thereof. The patient record generally has fields which can include patient identification, patient medication profile, patient allergy profile, patient diagnosis profile, and patient insurance profile. Upon receipt of either the entire patient record or select portions thereof, the entire patient record or the select portions can be stored in the memory 21 (database 22) of the pharmacy group management server 15.

A queue 57 receives the digital image and holds the digital image for a prescription order requirements entry and release verification by a remote pharmacy pharmacist. A drug conflict analyzer 59, responsive to the prescription order requirements and data contained within the patient record, can analyze the prescription order requirements against the patient medication profile, the patient allergy profile, the patient diagnosis profile, and patient insurance profile, and a drug interaction profile, to determine if a conflict exists. If no conflict is found, a dispensing initiator 61 positioned to receive the medication inventory for each of the pharmaceutical storage and electronic dispensing carts 30 and responsive to the release verification performed by the remote pharmacy pharmacist, can transmit individual facility patient pharmaceutical dispensing instructions to the respective pharmaceutical storage and electronic dispensing cart 30 over the communication network 18 to thereby initiate patient medication dispensing.

A patient billing tracker 63, responsive to patient medication dispensing from the respective pharmaceutical storage and electronic dispensing cart 30, can provide separate billing records for each of a plurality of patients at the plurality of long-term care facilities 12. A claims processor 65, responsive to billing records from the patient billing tracker 63 and a date reference signal, can submit medication claims for each patient to either a reimbursement provider or a patient representative, or both. The claims processor 65 can also consolidate billing data for each long-term care patient, indexed by reimbursement provider, and submit the medication claims to each respective reimbursement provider.

An inventory tracker 67 can maintain the medication inventory for each of the pharmaceutical storage and electronic dispensing carts 30. An inventory replenisher 69 is positioned to receive the medication inventory from the inventory tracker 67, and responsive to the medication inventory decreasing below a minimum threshold level, to notify pharmacy personnel associated with the remote pharmaceutical dispensing and storage facility 40 of a replenishment requirement for at least one of the pharmaceutical storage and electronic dispensing carts 30.

A medication dispensing apparatus administrator 71, responsive to an input from pharmacy personnel, can selectively remotely control functions available to facility medical personnel from the terminal of the pharmaceutical storage and electronic dispensing cart 30, over the communications network, to thereby remotely provide training to the facility medical personnel. A medication dispensing apparatus imager 73, responsive to video signals from the video input device 31, can display a video image of facility medical personnel and functional components of the pharmaceutical storage and electronic dispensing cart 30 over the communications network 18, to also remotely provide training to the facility medical personnel and for remote, real-time, troubleshooting the pharmaceutical storage and electronic dispensing cart 30.

It is important to note that although embodiments of the present invention have been described in the context of a fully functional system, those skilled in the art will appreciate that the mechanism of the present invention and/or aspects thereof are capable of being distributed in the form of a computer readable medium of instructions in a variety of forms for execution on a processor, processors, or the like, and that the present invention applies equally regardless of the particular type of signal bearing media used to actually carry out the distribution. Examples of computer readable media include: nonvolatile, hard-coded type media such as read only memories (ROMs) or erasable, electrically programmable read only memories (EEPROMs), recordable type media such as floppy disks, hard disk drives and CD-ROMs, and transmission type media such as digital and analog communication links.

For example, in an embodiment of the present invention, the system 10 includes a computer readable medium comprising a set of instructions that, when executed by a computer, such as, for example, group management server 15, remote pharmacy group server 40, or a combination of the both, cause the computer to establish remote communications between a remote pharmacy 16 and between each of a plurality of pharmaceutical storage and dispensing apparatus 30 having a memory associated therewith and a plurality of medication dispensing cartridges, to perform instructions to manage pharmaceutical operations. The instructions can include those for registering at least one patient for each of a plurality of long-term care facilities 12 in a database of residents for the long-term care facility 12 associated with a pharmaceutical storage and dispensing apparatus 30 located at that long-term care facility 12. The instructions include those for receiving a digital image of an actual pharmaceutical prescription order containing patient prescription requirements, queuing the pharmaceutical prescription order for examination by a remote pharmacy pharmacist associated with the remote pharmacy 41, analyzing the patient prescription requirements against parameters such as a patient medication profile, a patient allergy profile, a patient diagnosis profile, a patient insurance profile, and a drug interaction profile, to determine if a conflict exists. The instructions can include those for storing in memory of each pharmaceutical storage and dispensing apparatus 30 at least one medication type, an amount to be dispensed, and a medication dispensing time, and those for maintaining a record of medication dispensed and an inventory of medication remaining in each cartridge of each pharmaceutical storage and dispensing apparatus 30. The instructions can also include those for transmitting the patient prescription requirements to the pharmaceutical storage and electronic dispensing cart 30, and dispensing medication in response to the patient prescription requirements for each patient registered to the pharmaceutical storage and dispensing apparatus 30. The instructions can further include those for submitting medication claims to a reimbursement provider for each patient, providing separate billing records for each registered patient at each of the plurality of long-term care facilities 12, and consolidating billing data for each registered patient at each of the plurality of long-term care facilities 12, the billing data preferably indexed by reimbursement provider.

FIG. 8C illustrates the typography of database software according to an embodiment of the present invention. The system user 351 is identified by a user ID related to the pharmacy group 353 by a pharmacy group ID. A facility 355 identified by a facility ID is also related to the pharmacy group 353 by the pharmacy group ID. A facility drug/medication dispensing cart 357 is related to the facility 355 by the facility ID and to an individual drug cart 359 (identified by cart ID) by such cart ID. A drug cart inventory 361 identified by nde (National Drug Counsel) and having pharmaceuticals identified by medication ID is related to the drug cart 359 by the cart ID. A facility formulary 363 is related to the pharmacy group 353 through the preferred drug 365 by the group ID, is related to the preferred drug 365 by a medication ID, and is related to the facility 355 by the facility ID. A pharmacy 367 identified by nabp (National Association of Boards of Pharmacy identification) is related to the pharmacy group 353 by the group ID. A patient facility residency 369 identified by start date is related to a patient 371 identified by patient ID by such patient ID) and is related to a facility room 373 (identified by room number) by such room number. The patient 371 can be related to the pharmacy group 353 by the group ID. The facility room 373 is related to the facility 355 by the facility ID. A patient insurance 375 identified by coverage date is related to insurance 377 (identified by insurer ID) by such insurer ID, and is related to the patient 371 by the patient ID. Patient allergy 379 identified by allergy ID, patient diagnosis 381 identified by icd9 cd (diagnosis profile), and patient medication profile 383 identified by ndc are each related to patient 371 by the patient ID. A prescription 385 identified by script ID is related to the pharmacy 367 by the nabp, is related to prescriber 389 (identified by prescriber ID) by such prescriber ID, and can be related to the patient 371 by the patient ID. Prescription detail 391 identified by script fill number is related to the prescription 385 by the script ID. Claim 393 identified by claim number is related to the prescription detail 391 by the script fill number and to the pharmacy group 353 by the group ID, is indirectly related to the patient prescription 385 by the script ID and the pharmacy 367 by the nabp, and can be related to the patient 371 by the patient ID. A drug utilization review (DUR) 395 is related to the prescription 385 by the script ID, the patient 371 by the patient ID, and is indirectly related to the pharmacy 367 by the nabp. DUR dose check 396, DUR drug allergy 397, DUR dup therapy 398, and DUR drug interaction 399 are identified by drug index number and related indirectly through the DUR 395 to the pharmacy 367 by the nabp, prescription 385 by the script ID and patient 371 by the patient ID. Database items (not shown) not having a primary relationship include wholesale drug price identified by ndc, price code, icd9 cd, medication roa, medication dose form, and medication frequency.

FIG. 9 illustrates a system 10' of enhanced pharmaceutical operation services for a long-term care facility 12' according to an embodiment of the present invention that includes an array of incoming data servers, a database server, and automated dispensing system servers each having a memory therein to store and process data therein to thereby define a long-term care facility pharmacy group management server 15'. The long-term care facility pharmacy group management server 15' can manage pharmaceutical operations in various managed care facilities and/or correctional facilities, such as, for example, long-term care facility 12.' The long-term care facility 12' includes at least one, but preferably a plurality of automated dispensing systems or machines 30' to remotely dispense medications, and a preferably centrally located image capturing device or devices, such as, for example, fax machine 14' and scanner 14" connected to a workstation computer, to provide an image of a patient prescription order. The system 10' additionally can include at least one but preferably a plurality of remote pharmacy group computers 40' positioned remote from the long-term care facility 12.' The remote pharmacy group computers 40' are in communication with the long-term care facility pharmacy group management server 15' and the plurality of automated dispensing systems or machines 30,' through a communication network, to process the patient prescription orders and to provide dispensing instructions to the automated dispensing systems or machines 30'. The remote pharmacy group computers 40' are preferably located in a remote pharmaceutical dispensing and storage facility at a location remote from both the long-term care facility 12' and the pharmacy group management server 15.' Long-term care facility pharmacy management software 20 can be stored in the memory of the servers defining the long-term care facility pharmacy group management server 15' to manage pharmaceutical operations in long-term care facility 12.' Further, at least portions of the software 20 can be stored in the remote pharmacy group computers 40' and in the automated dispensing systems or machines 30,'

Figure 6:
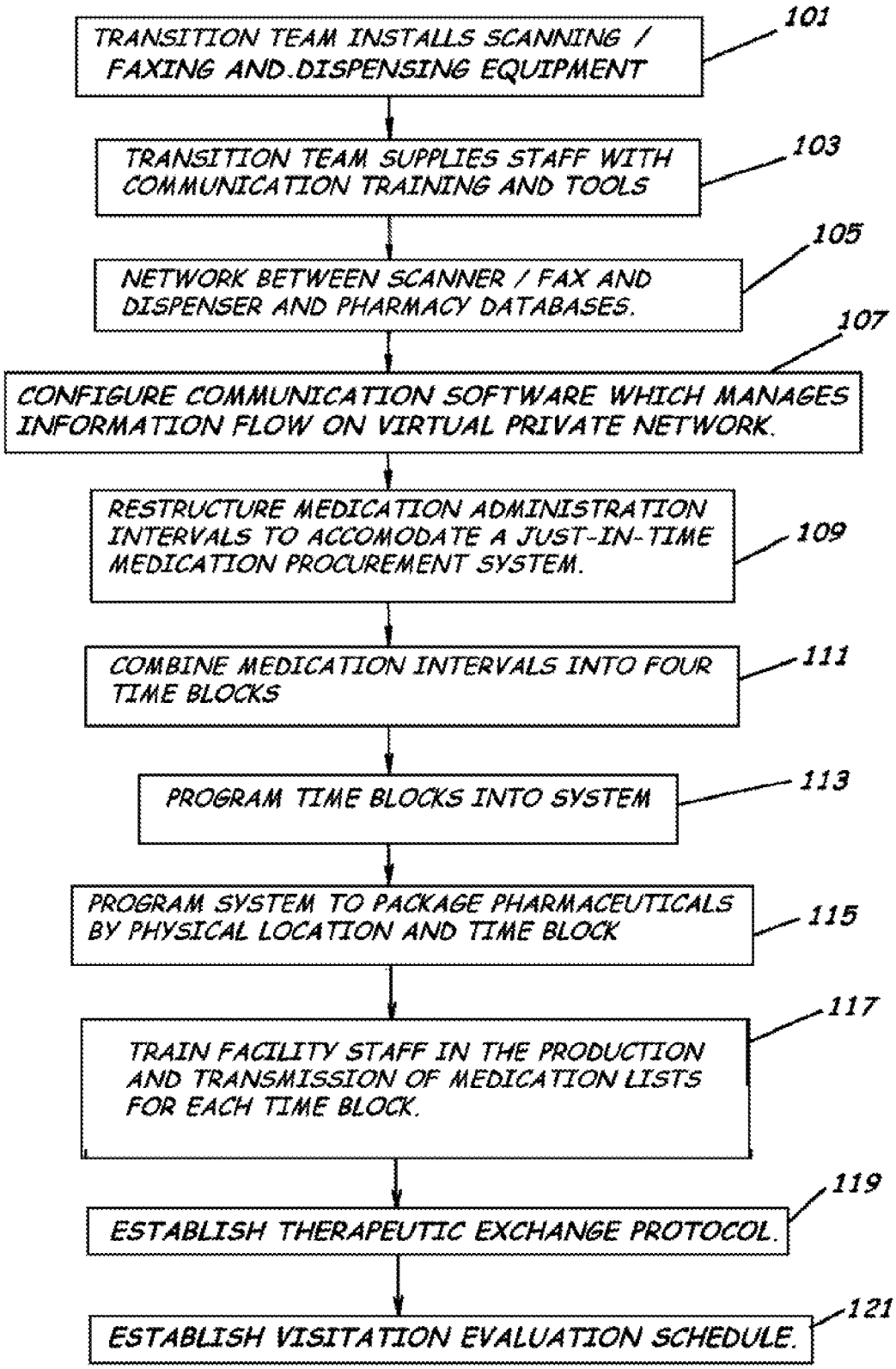
FIG. 6 is a schematic flow diagram of a method of enhanced pharmaceutical operations in a long-term care facility according to an embodiment of the present invention.

As perhaps best shown in FIG. 6, generally methods of delivering pharmaceutical operation services have three main components for implementation, namely restructuring communication methods and intervals, automating medication procurement and distribution, and evaluation of routine, e.g., weekly, visits to assess system performance and maintenance. When a long-term care facility 12 desires to implement an embodiment of a system 10 (FIGS. 1A-1B) to enhance pharmaceutical operations, a transition team from the remote pharmacy staff, for example, or from a combination of remote pharmacy staff and long-term care facility staff, for example, can be used to assist in changing the existing procedures of using pharmaceutical services and dispensing medications for the long-term care facility 12 and in implementing the new system 10, software 20, and methods of embodiments of the present invention.

Restructuring communication methods and intervals, for example, can include installing (block 101) facsimile, scanning, or other document processing equipment 14 (FIG. 3) to scan physician prescription orders and to transmit them to the remote pharmacy group server 40 or the pharmacy group management server 15 via a virtual private network ("VPN") 18 (see FIG. 7). Medication errors can be reduced when the pharmacy staff at the remote pharmacy are able to view exact images of orders (see also FIGS. 8A-8B). Voice communication over telephone lines can be error prone due to language barriers and transcription errors. Direct imaging allows the pharmacist to interpret the medication orders in the same way as the facility staff. Should an error be made, then one of the healthcare professionals is more likely to discover the error if direct imaging is in place. For example, allowing the pharmacist to read a copy of the original document insures that at least two healthcare professionals have reviewed the order, namely the nurse and the pharmacist. These separate order reviews lead to separate documentation by the nurse and the pharmacist. If these two document sources do not match, then the nurse and pharmacist can discuss the order and clarify with the prescriber, if necessary.

The methods also supply long-term care facility staff with the training and tools (block 103) to allow the remote pharmacy to communicate with the facility 12 at the end of each medication administration interval for administration of medication to the residents of the long-term care facility 12. Because the communication is built into or included with the medication distribution procedures, the tools, for example, allow this communication to occur frequently and without requiring additional facility staff time. More frequent communications allow the system 10, software 20, and methods to reduce errors due to miscommunication and misinterpretation of medication orders, and tools such as medication pass lists (not shown) and new or changed order reports (not shown), as understood by those skilled in the art, result in better synchronization between the pharmacy and the facility documentation. Medication pass lists are generally utilized to document delivery of medication to a patient and include the time, quantity, method of dispensing, and health professional dispensing the medication. By supplying or communicating such medication pass lists to the pharmacist, the pharmacist is provided a unique methodology to determine if the medication was dispensed according to instructions provided to the pharmaceutical storage and dispensing apparatus 30 and if the medication distribution procedures are being adhered too. New or changed order reports are generally used to document changes in a patient medication order and include changes in the time, quantity, or method of dispensing medication. By supplying or communicating such changed order report to the pharmacist, the pharmacist is provided yet another methodology of determining if the medication dispensing instructions provided to the pharmaceutical storage and dispensing apparatus 30 coincide with that which the facility medical personnel believe to be the instructions provided by the patient prescription order. Any discrepancy can be discussed between pharmacy member and facility medical personnel, enhancing quality control. Advantageously, use of standardized medication pass lists and new or changed order reports provided or approved by the pharmacy allows enhanced communication between pharmacy and facility medical personnel, not otherwise available if the pharmacy had to review medication pass lists and new or changed order reports having a different format for each long-term care facility 12.

Further, remote pharmacy personnel, through the long-term care facility pharmacy group management server 15 or a remote pharmacy group server 40, can dial-up or otherwise remotely access the dispensing cart 30 through the communication network 18 and perform virtual "face-to-face" training of facility medical personnel along with other tasks such as, troubleshooting, packaging medications, and all other functions that can be performed by the dispensing cart 30, itself. In an embodiment of the present invention having video input device 31 (FIG. 2), this virtual "face-to-face" can further be in the form of a videoconference, including audio communications, whereby pharmacy personnel can monitor instantaneously the actions of the facility medical personnel to provide real-time feedback and to verify results of actions taken by the facility medical personnel or functions performed by the dispensing cart 30. These features provide the facility medical personnel real-time help in learning and operating the dispenser cart 30 which advantageously provides for an acceptance level not attainable where such real-time support 24/7 is not available. Note, the video input device 31 can be mounted either to the dispensing cart 30 or adjacent the dispensing cart 30 such that pharmacy personnel can readily view, and thus help instruct, actions by facility medical personnel. In an embodiment of the present invention, the video input device 31 can include hardware such as, for example, servo motors, that will allow the device 31 to be remotely controlled to change viewing angle, to change focus, or to zoom in or out to better view the facility medical personnel or components of the dispensing cart 30.

Likewise, within the remote pharmacy facility, the pharmacy management software 20 can be networked to communicate with both the long-term care facility document processor 14, e.g., fax machine, scanner, or image capture device, and the pharmaceutical storage and dispensing machines or cart 30, and the optional video input device 31, at the long-term care facility 12 (block 105). The software 20 and methods can be configured (block 107) to manage information flow on the VPN 18 between the long-term care facility document processor 14, long-term care facility pharmaceutical storage and dispensing machines or cart 30, and one or more pharmacy database 22 associated with the software 20. The software 20 and methods, thus, allow the remote pharmacy and the long-term care facility 12 to communicate in real time or near real time and provide near real time medication fulfillment for the long-term care facility residents. The software 20 and methods also can manage an unlimited number of long-term care facilities 12 (for example, via a plurality of remote pharmacy groups (see FIG. 1A-1B)) within embodiments of the system 10 of the present invention and can be assessed/managed by remote pharmacy staff by use of the VPN.

Figure 5:
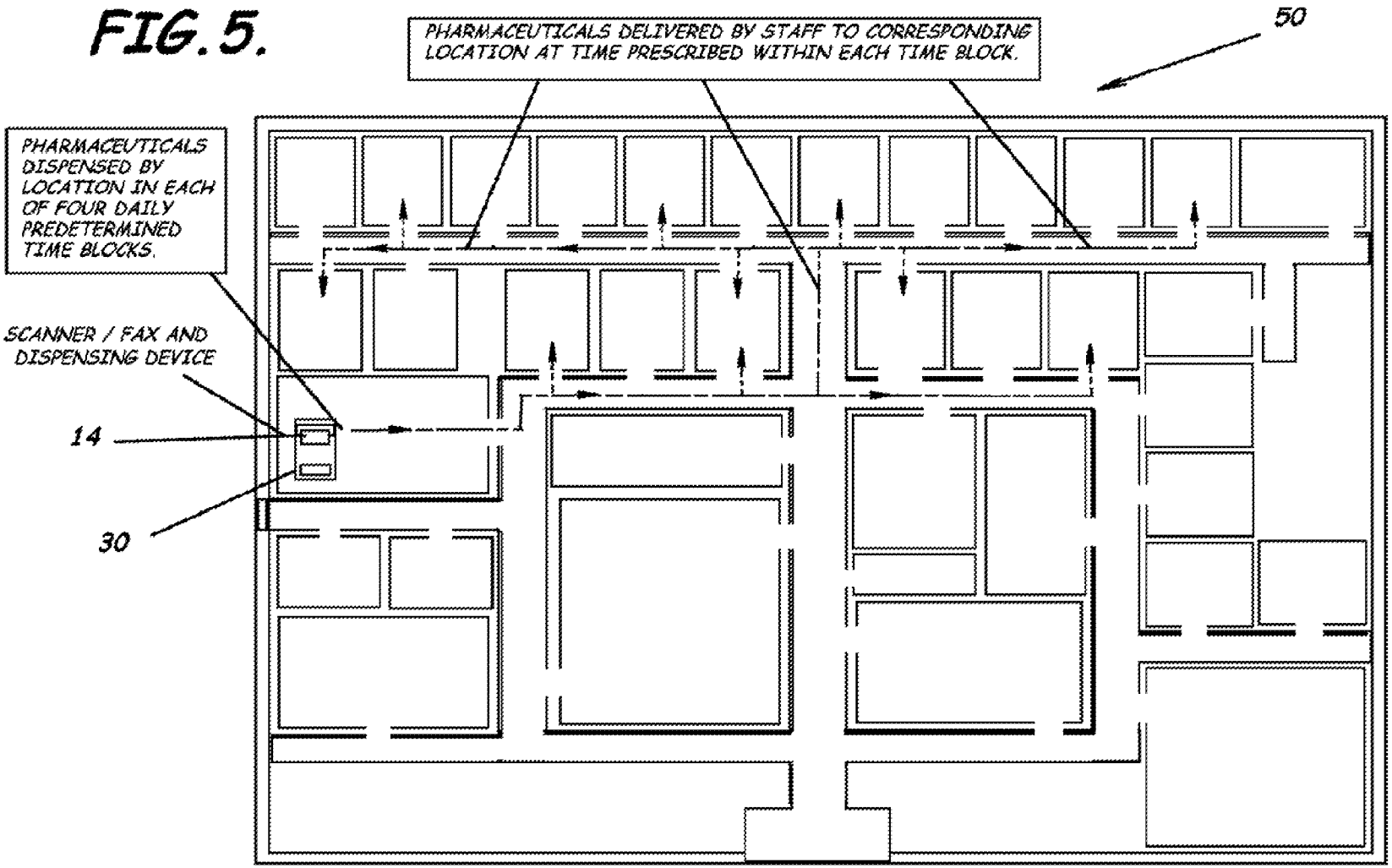
FIG. 5 is a top plan view of a long-term care facility of a system and method of enhanced pharmaceutical operations in long-term care facilities according to an embodiment of the present invention.

For automating medication procurement and distribution, for example, the transition team can aid in restructuring the medication administration intervals (block 109) to accommodate more of a just-in-time medication procurement system to significantly reduce waste and risk of errors (see also FIG. 5). The medication intervals can be combined into a preselected number of medication pass time blocks (block 111), e.g., four pass times (breakfast 2400-0600, AM 0600-1030, Noon 1030-1430, and HS 1830-2400). Each block of time has specific medication administration times within the block (see also FIG. 5). Once time blocks are established, these time blocks are programmed (blocks 113 and 115) into the pharmaceutical storage and dispensing machines or carts 30 so that pharmaceuticals or medications (FIG. 4B) are packaged by physical location within the long-term care facility 12 and by time block and loaded into caddies or trays 35 (FIG. 4A) associated with the dispensing carts 30. This procurement method significantly reduces long-term care facility staff time spent on medication procurement, e.g., by up to 50%, and reduces medication errors. Long-term care facility staff can be taught (block 117) how to produce medication lists for each time block. The medication list is used as a road map for the medication administration interval and can be transmitted via the VPN 18 to the remote pharmacy. This method enhances communication by requiring or insuring communication between the remote pharmacy staff and the long-term care facility staff at least four times per day with little added time commitment by either party.

Additionally, the transition team can meet with facility physicians to establish a type of automated therapeutic exchange protocol (block 119). This protocol can be managed by the remote pharmacy management software 20 and allows the long-term care facility and remote pharmacy to manage formulary management programs through the VPN 18 in a real time or near real time manner. The therapeutic exchange protocol streamlines the inventory of each of the plurality of pharmaceutical storage and electronic dispensing carts 30, reduces wasted medication, and reduces costs for payors.

Further, periodic or preselected visits (block 121) to each long-term care facility within the system 10 to assess system performance and maintenance can be conducted by the remote pharmacy staff. This can enhance communication and enhance performance assessments within the system 10. Dispensing carts 30, document processors 14, software 20, medication inventory, and other elements of the system 10 also can be maintained during these visits as well. For example, medications that cannot be packaged by a pharmaceutical storage and electronic dispensing cart 30 can be reviewed and reordered, if needed.

As perhaps best shown in FIGS. 7-8B, in operation, to start new medications nurses can have first dose privileges. If a medication is for a new resident in the long-term care facility 12, then the remote pharmacy or an on-call pharmacist can be notified so the resident can be added to a database 22 of residents for the particular long-term care facility 12 associated with the pharmaceutical storage and dispensing cart 30 located at that facility. A pharmacist at the remote pharmacy can enter prescription information from a faxed or scanned physician's order into the pharmacy group management software 20. More specifically, the pharmacist receives the digital faxed/scanned image (block 131) of the prescription for a patient. Based upon the information provided with the prescription, the pharmacist then enters into the software 20 the location of a remote pharmacy (block 133), the name of or identification for the facility (block 135), the patient information (block 137), and the preferred drug (block 139). The pharmacist further enters (block 141) details of dosage, route of administration, frequency and duration of the prescription. The pharmacist further enters (block 143) the quantity to be dispensed and prescribing physician information.

The software 20 can then perform (block 145) a drug utilization review (see also FIG. 7). The above described information is then sent to a checking queue (block 147) whereby the pharmacist checks (block 149) the physical prescription for correctness. The software 20 then can determine if the drug to be dispensed is in stock in the pharmaceutical storage and dispensing cart 30. If the software 20 determines that the medication is stocked in the dispensing cart 30, then it can send the prescription information to the dispensing cart 30 (block 151) instead of printing a traditional prescription label. The cart 30 can then dispense the medication during the scheduled administration time. If the medication is not stocked in the dispensing cart 30, then a prescription label can be produced. The prescription can then be filled and delivered in a traditional way to the long-term care facility 12, e.g., by the vehicle V. The traditional way, for example, can also be used for non-oral solid medication such as liquids, creams, inhalers, and injectables as well, e.g., daily deliveries, as the pharmaceutical storage and electronic dispensing carts 30 often do not dispense these items.

Advantageously, embodiments of the present invention also include methods of increasing or generating revenue from a plurality of long-term care facilities 12 being devoid of an on-location pharmacy. For example, as perhaps best shown in FIG. 11, a method includes the steps of providing a pharmacy remote from a plurality of long-term care facilities (block 161) to define a long-term care facility remote pharmacy 41, positioning at least one pharmaceutical storage and dispensing apparatus 30 in each of the plurality of long-term care facilities 12 (block 163) to store and dispense pharmaceuticals to a patient living therein, each apparatus 30 preferably having at least one removable medicine cartridge. Remote communications are established (block 165) between each pharmaceutical storage and dispensing apparatus 30 and the remote pharmacy 41. Patients can then be registered (block 167) for each of the plurality of long-term care facilities 12 in a database of residents of the long-term care facility 12 associated with a respective pharmaceutical storage and dispensing apparatus 30, the database preferably stored in memory 21 of a data processing and management computer, such as, for example group management server 15. At least one medication type and amount to be dispensed (block 169) and a medication dispensing time (block 171) can be remotely programmed into each pharmaceutical storage and dispensing apparatus 30. Medication is then dispensed (block 173) according to patient prescription requirements for each associated registered patient. An inventory is maintained (block 175) of the medication dispensed and medication remaining in the pharmaceutical storage and dispensing apparatus. Advantageously, the method can include providing separate billing records (block 177) for each of the patients at each of the plurality of long-term care facilities 12. Billing data can then be consolidated for each of the patients (block 179) at each of the plurality of long-term care facilities. Medication claims can then be submitted to a reimbursement provider (block 181) organized by patient, grouped into categories, supplied in a batch form for each registered patient.

Figure 12A:
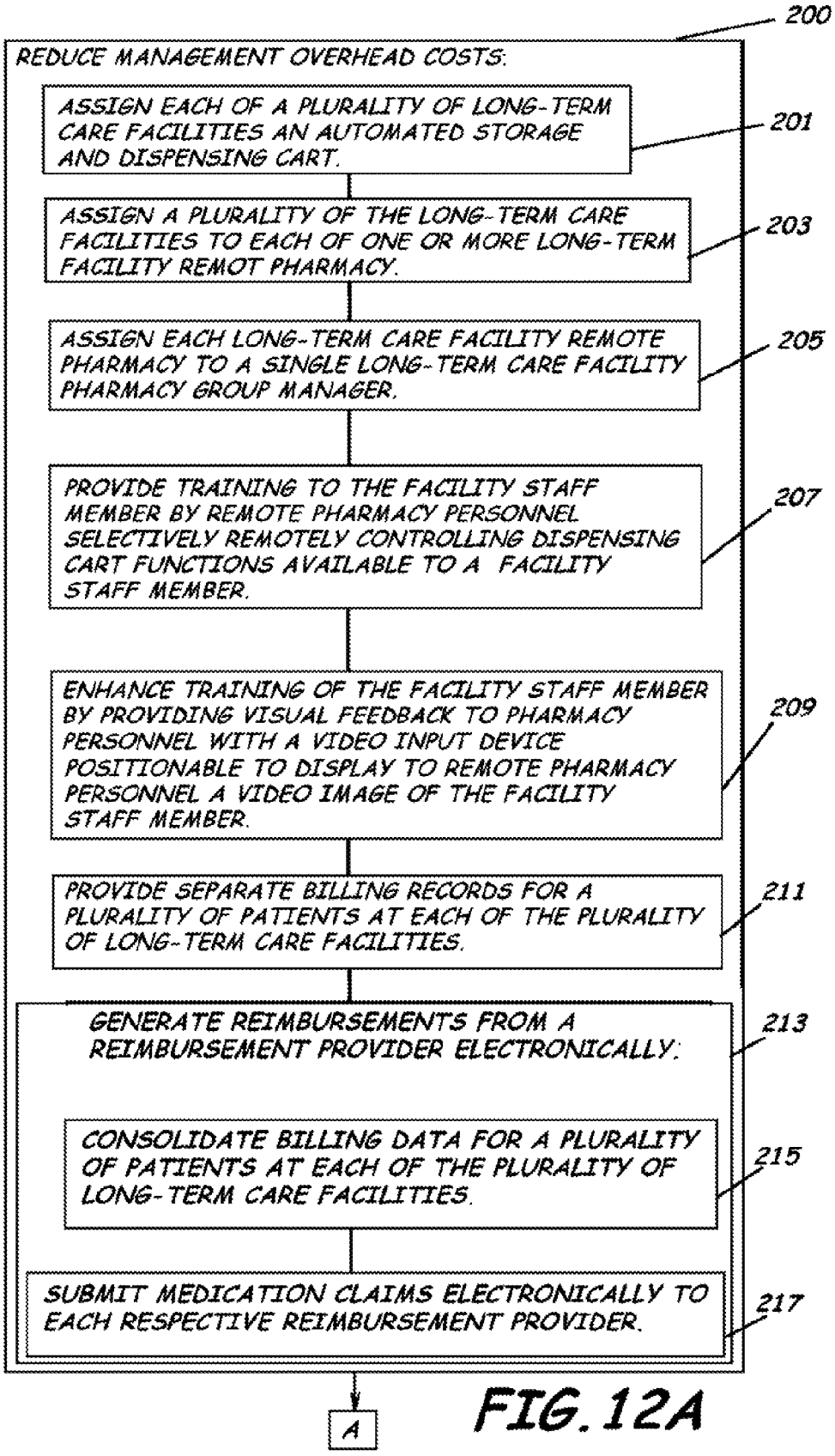
FIGS. 12A-C are schematic flow diagrams of a method of increasing sales to and generating revenue from a plurality of long-term care facilities being devoid of an on-location pharmacy according to an embodiment of the present invention.
Figure 12B:
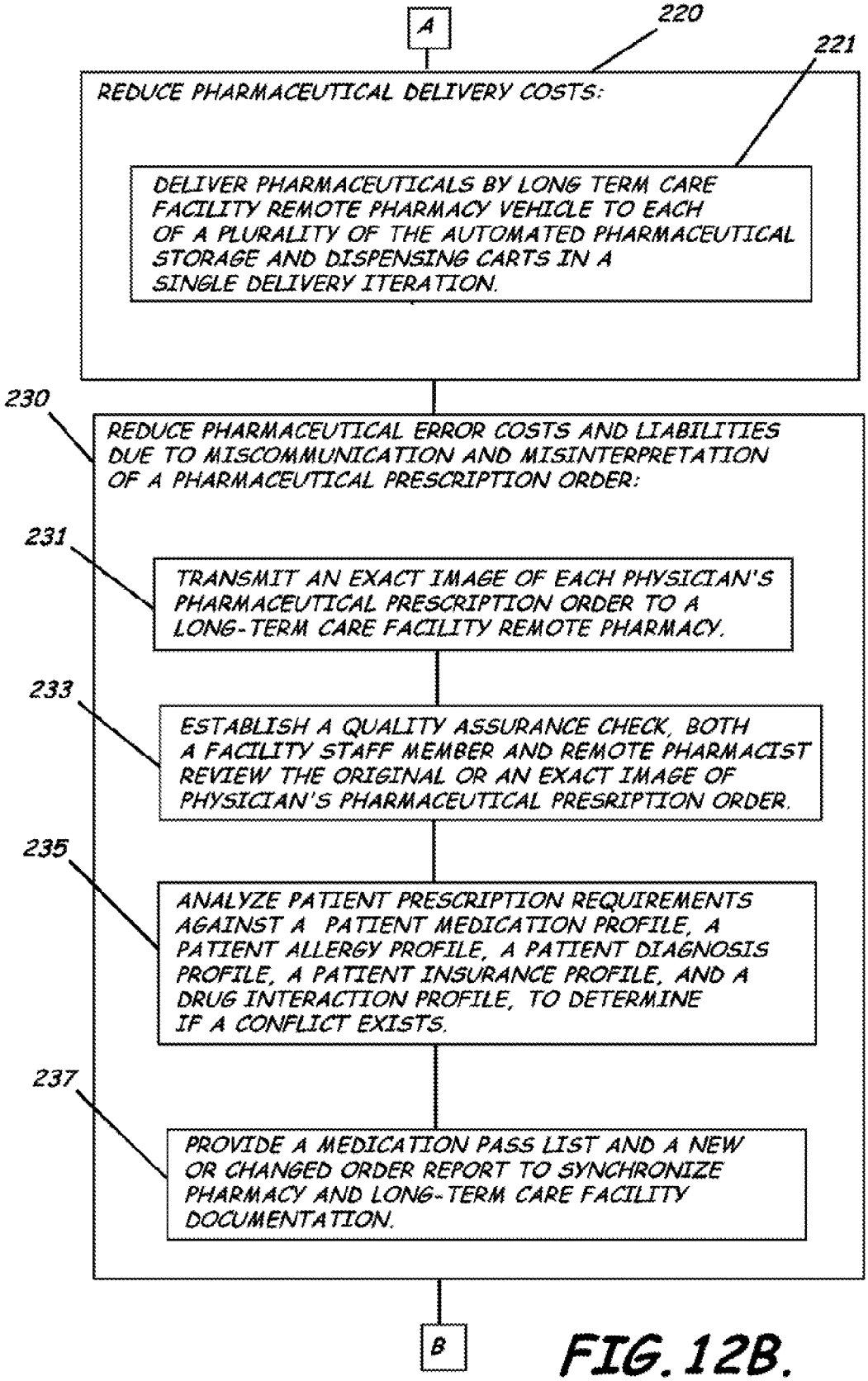
Figure 12C:
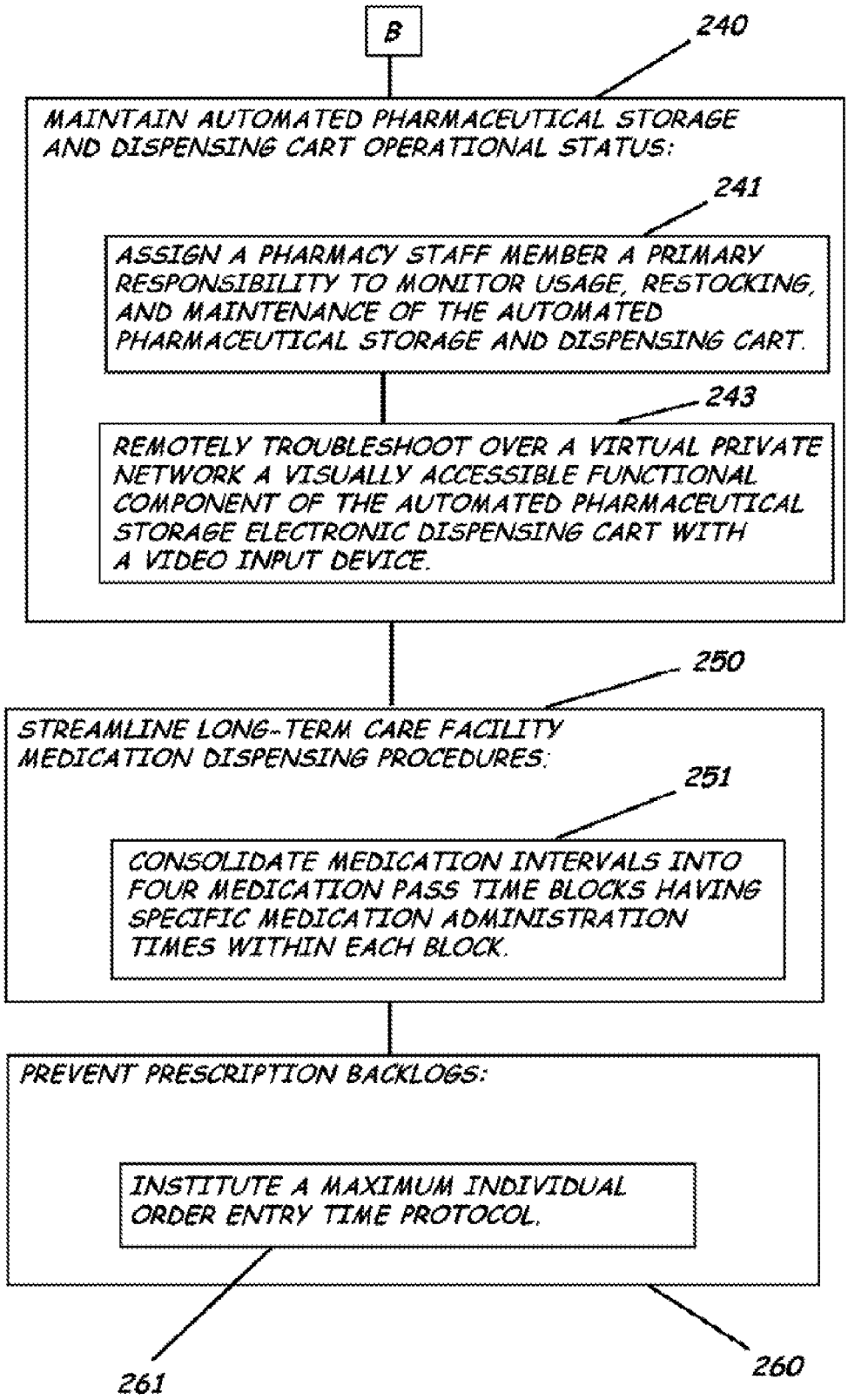

Also for example, as perhaps best shown in FIGS. 12A-C, a method of generating revenue from a plurality of long-term care facilities each devoid of an on-location pharmacy generally includes the steps of reducing management overhead costs (block 200), reducing pharmaceutical delivery costs (block 220), reducing pharmaceutical error costs and liabilities due to miscommunication and misinterpretation of a pharmaceutical prescription order (block 230), maintaining automated pharmaceutical storage and dispensing cart operational status (block 240), streamlining long-term care facility medication dispensing procedures (block 250), and preventing prescription backlogs (block 260).

Management overhead costs can be reduced by assigning each of the plurality of long-term care facilities 12 at least one automated pharmaceutical storage and dispensing cart 30 (block 201), assigning a plurality of the long-term care facilities 12 to each of at least one long-term care facility remote pharmacy 41 (block 203), and assigning the at least one long-term care facility remote pharmacy 41 to a single long-term care facility pharmacy group manager (block 205). This hierarchal management and supply structure allows pharmacy group management to continuously monitor multiple long-term care facilities 12 for a preselected region and to provide real-time management of pharmaceutical distribution and resupply. Further, costs can be reduced by remotely providing training (block 207) by selectively remotely controlling functions available to a facility staff member from a terminal of the pharmaceutical storage and electronic dispensing cart 30 over a communications network 18. This allows for the provision of a virtual on-site face-to-face training session to help a facility staff member having difficulties interfacing with the pharmaceutical storage and dispensing cart 30, thus preventing the need for an actual on-site visit and allowing provision of such service 24 hours a day, 7 days a week, generally not otherwise available. Training of facility staff members can be enhanced (block 209) by providing pharmacy personnel with audio and with visual feedback through a video input device 31 (FIG. 2) positioned adjacent to and preferably interfaced with the pharmaceutical storage and electronic dispensing cart 30 and positionable to display over the network 18 a video image of the facility staff member. Costs can further be reduced through the use of software 20 that can interface with the pharmaceutical storage and electronic dispensing cart 30 to both providing separate billing records for a plurality of patients at each of the plurality of long-term care facilities (block 211), and generate reimbursements from a reimbursement provider electronically (block 213). The reimbursements can be generated by consolidating billing data for a plurality of patients at each of the plurality of long-term care facilities 12 (block 215) for submission to a respective same reimbursement provider, followed by submitting medication claims electronically (block 217) to each respective reimbursement provider for each of the plurality of patients. This allows for efficient batch-type processing of patient claims by each reimbursement provider.

Pharmaceutical delivery costs can be reduced through the use of a dedicated remote pharmacy vehicle V for delivering pharmaceuticals to multiple long-term care facilities 12 to resupply each facilities pharmaceutical storage and dispensing carts 30 and to provide those pharmaceuticals according to the patient prescription requirements and not provided by each respective pharmaceutical storage and electronic dispensing cart 30, preferably all in a single delivery iteration. This allows for establishing regular delivery routes resulting in efficient use of the vehicular asset and pharmacy personnel.

Pharmaceutical error costs and liabilities due to miscommunication and misinterpretation of a pharmaceutical prescription order can be reduced through use of a procedure whereby instead of having facility staff members review a physician's prescription order and transmit extracted information, facility staff members can transmit an exact image of each physician's pharmaceutical prescription order (block 231) from a pharmaceutical document processor 14 associated with a pharmaceutical storage and electronic dispensing cart 30 over the network 18 to a respective long-term care facility remote pharmacy 41. This procedure allows for establishment of a quality assurance check (block 233) whereby both the facility staff member and the remote pharmacist can both review the original or an exact image of the original physician's pharmaceutical prescription order. This redundancy reduces errors in interpretation of the physician's prescription order. Patient prescription requirements can then be analyzed (block 235) against a patient medication profile, a patient allergy profile, a patient diagnosis profile, a patient insurance profile, and a drug interaction profile, to determine if a conflict exists. Further, a standardized Medication Pass List (not shown) and a New or Changed Order Report (not shown) can be provided (block 237) to synchronize pharmacy and long-term care facility documentation. This synchronization prevents waste and helps ensure accountability.

Maintaining operational status of an automated pharmaceutical storage and dispensing cart 30 can be an extremely significant issue in an automated pharmaceutical dispensing operation. In the preferred embodiment of the present intention, pharmacy staff members rather than facility staff members are assigned a primary responsibility to monitor usage, restocking, and maintenance of the pharmaceutical storage and dispensing cart 30 (block 241). Establishing accountability for the carts 30 with pharmacy personnel has led to significant improvements in operational status. Further, implementing a procedure whereby pharmacy personnel can remotely troubleshoot over the communication network 18 (block 243) a visually accessible functional component of the pharmaceutical storage electronic dispensing cart 30 with use of a video input device 31 (FIG. 2) positioned adjacent to and preferably interfaced with the pharmaceutical storage and electronic dispensing cart 30. In an embodiment of the present invention, the video input device 31 can be connected to or adjacent the pharmaceutical storage and electronic dispensing cart 30 via a flexible and/or snake mount or other suitable connection known to those skilled in the art, such as, for example, a USB cable, telephone cable, coaxial cable, optical cable, or wireless transceiver. The video input device 31 can thus be positionable by facility staff members or other personnel to display a realtime video image of the visually accessible functional component of the pharmaceutical storage and electronic dispensing cart 30, allowing for real-time troubleshooting of the cart 30. Further, the video input device 31, can be remotely controlled to change viewing angle, to change focus, or to zoom in or out to better view the component or components of interest and to monitor actions of the facility medical personnel or other on-station pharmacy personnel requested to move a panel or component or to perform the repair. This allows pharmacy personnel to maintain supervision and thus control, over any non-standard mechanical manipulation or repair of the cart 30.

Streamlining long-term care facility medication dispensing procedures can be accomplished by consolidating medication intervals (block 251). In the preferred embodiment of the present intention, medication intervals are consolidated into four medication pass time blocks, each block having specific medication administration times within the respective block. This has resulted in improved medication dispensing efficiency, reduced facility staff member workload and potentially significantly reduced costs for the long-term care facility 12, and thus, an increase in acceptance of the pharmaceutical storage and electronic dispensing carts 30.

An inherent problem with having to receive electronic images of the physician's prescription order is the potential for a backlog due to prescription order entry difficulties. Due to the reduced number of medication pass time blocks, receiving and processing prescription orders can be time critical. In a just-in-time type system, a prescription order entry difficulty caused by as little as a single entry problem could potentially cause a late arrival of the prescription order resulting in a late delivery of patient medication. Institution of a maximum individual order entry time protocol (block 261) prevents such prescription backlogs due to prescription order entry difficulties. This protocol allows the remote pharmacy 41 to accommodate massive numbers of incoming prescription orders.

As illustrated in FIGS. 1-12C, and as described above, embodiments of the present invention includes a method of providing pharmaceutical services to long-term care facilities 12 including providing a pharmacy remote from a plurality of long-term care facilities 12 to define a long-term care facility remote pharmacy, restructuring long-term care facility staff procedures for communication between the long-term care facility staff and the long-term care facility remote pharmacy, restructuring medication procurement and resident medication distribution procedures within a plurality of long-term care facilities, installing a pharmaceutical storage and electronic dispensing machine or cart 30 at each of the plurality of long-term care facilities 12 to be used by the long-term care facility staff, and visiting each of the plurality of long-term care facilities 12 on a preselected frequency, e.g., from the remote pharmacy, to assess performance and enhance communication.

By implementing these methods, a system 10, and software 20 of embodiments of the present invention, shift-change medication counts can be eliminated or significantly reduced, medication preparation and pass times can be reduced, and drug/medication destruction can be significantly reduced. Also, long-term care facility staff can have more free time due to the planning and implementation of a structure procedure of embodiments of the present invention. In turn, care of the residents can be enhanced by allowing staff to have more time for care of residents instead of on medication preparation and passing time, documentation can be improved, risk of liabilities can be reduced, risk of errors and stolen medications can be reduced, and communication between long-term care facility staff and pharmacy staff can be enhanced. Additionally, embodiments of a system 10, software 20, and methods allow a long-term care facility 12 to reduce operational costs and staffing, if desired. In turn, residents and payors can save money, and residents can have better care.

This application is related to U.S. patent application Ser. No. 11/818,416, filed Jun. 14, 2007, titled "System and Software of Enhanced Pharmaceutical Operations in Long-Term Care Facilities and Related Methods"; U.S. patent application Ser. No. 10/944,993, filed Sep. 20, 2004, titled "System and Software of Enhanced Pharmaceutical Operations in Long-Term Care Facilities and Related Methods"; and U.S. Provisional Patent Application Ser. No. 60/516,678, filed on Nov. 3, 2003, titled "System and Software of Enhanced Pharmaceutical Operations in Long-Term Care Facilities and Related Methods," each incorporated herein by reference in its entirety.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That claimed is:

1. A computer implemented method of remote pharmacy management of a plurality of pharmaceutical storage and electronic dispensing carts, the method comprising:

[scheduling on one or more computers one or more preselected time intervals for dispensing of at least one medication through each of a plurality of pharmaceutical storage and electronic dispensing carts according to patient specific prescription requirements, each of the plurality of pharmaceutical storage and electronic dispensing carts having a plurality of different medications stored in bulk therein and being located at a long term care facility positioned remote from the one or more computers;] *scheduling by one or more computers, dispensing of at least one medication of a plurality of medications stored in bulk on one of a plurality of pharmaceutical storage and electronic dispensing carts located at a plurality of long term care facilities, the dispensing performed through the one of a plurality of pharmaceutical storage and electronic dispensing carts according to patient specific prescription requirements;* controlling [from], *by* the one or more computers, each of the plurality of pharmaceutical storage and electronic dispensing carts;

[individually] retrieving, responsive to the controlling from the one or more computers, *the* at least one medication of the plurality of [different] medications [stored in bulk], *based on the schedule provided by the one or more computers*;

loading, responsive to the controlling from the one or more computers, the at least one medication into one of [the] *a* plurality of disposable individual patient dosing packages to thereby package the at least one medication in the one of the plurality of disposable individual patient dosing packages;

dispensing, responsive to the controlling from the one or more computers, the packaged one of the plurality of individual patient dosing packages [into a container associated with the cart prior to the one or more preselected time intervals scheduled to thereby dispense medication by authorized medical personnel after separating the container from the cart when having the packaged one of the plurality of individual patient dosing packages therein according to patient specific prescription requirements;], *dispensed for authorized medical personnel to administer to patients;*

[receiving dispensing data to the one or more computers remote from each of the plurality of pharmaceutical storage and electronic dispensing carts, the dispensing data including which at least one medication was actually dispensed to a patient so that only medication actually dispensed is to be billed;]

processing, by the one or more computers, billing records including billing data for each of [the] *a* plurality of patients at each of the plurality of long-term care facilities based on [the received] dispensing data *received from each of the plurality of pharmaceutical storage and electronic dispensing carts*, the billing data including *indicia of which of the at least one medication was actually dispensed to a patient so that only medication actually dispensed is to be billed to a* reimbursement provider;

consolidating the billing data according to *the* reimbursement provider by the one or more computers to thereby generate reimbursements to be provided from one or more reimbursement providers, the billing data also including [billing] data for *indicating* medications actually dispensed to a respective patient from at least one of the plurality of pharmaceutical storage and electronic dispensing carts so that only medication actually dispensed is billed to the reimbursement provider; and submitting by the one or more computers separate consolidated reimbursement claims electronically to each respective reimbursement provider.

2. A computer implemented method as defined in claim 1, wherein the step of [controlling] *dispensing* includes dispensing the packaged *one of the plurality of individual patient dosing packages containing the* at least one medication into [the] *a* container *separable from the cart* during [the] *one or more* preselected time intervals prior to a predetermined schedule of distribution of medication dosages to the plurality of patients in each of the plurality of long-term care facilities.

3. A computer implemented method as defined in claim [2, wherein the step of receiving dispensing data further includes] *1, further comprising: receiving by the one or more computers,* dispensing data [of] *identifying* medications remaining stored in bulk in and not actually dispensed from a pharmaceutical storage and electronic dispensing cart.

4. A computer implemented method as defined in claim [2] *1*, wherein the step of consolidating billing data by reimbursement provider further includes consolidating billing data by patient at a long term care facility for each reimbursement provider, and wherein the step of submitting consolidated reimbursement claims includes electronically submitting the consolidated reimbursement claims to each respective reimbursement provider for each associated patient in batch format.

5. A computer implemented method as defined in claim 1, further comprises submitting from the one or more computers consolidated reimbursement claims for each patient to a patient representative.

6. A computer implemented method as defined in claim 1, wherein the step of consolidating billing data further includes consolidating billing data by long term care facility for each reimbursement provider.

7. A computer implemented method as defined in claim 1, wherein the consolidating step comprises consolidating billing data from a remote pharmacy, and wherein the consolidating step includes consolidating billing data with a plurality of additional billing data from a plurality of additional remote pharmacies.

8. A computer implemented method of remote pharmacy management of a plurality of pharmaceutical storage and electronic dispensing carts, the method comprising:

scheduling on a computer [one or more preselected time intervals for dispensing of at least one medication through each of a plurality of pharmaceutical storage and electronic dispensing carts, each of the plurality of pharmaceutical storage and electronic dispensing carts having a plurality of different medications stored in bulk therein and being located at a patient care facility;] *dispensing of at least one medication of a plurality of medications stored in bulk on one of a plurality of pharmaceutical storage and electronic dispensing carts located at a plurality of long term care facilities, the dispensing performed through the one of a plurality of pharmaceutical storage and electronic dispensing carts according to patient specific prescription requirements;* processing control data from a computer by each of the plurality of pharmaceutical storage and electronic dispensing carts;

[individually] retrieving, responsive to the control data, *the* at least one medication of the plurality of [different] medications [stored in bulk] *based on the schedule provided by the one or more computers*;

loading, responsive to the control data, the at least one medication into one of the plurality of disposable individual patient dosing packages to thereby package the at least one medication in the one of [the] *a* plurality of disposable individual patient dosing packages;

dispensing, responsive to the control data, the packaged one of the plurality of individual patient dosing packages [into a container associated with the cart to thereby dispense medication by authorized medical personnel after separating the container from the cart when having the packaged one of the plurality of individual patient dosing packages therein according to patient specific prescription requirements;], *dispensed for authorized medical personnel to administer to patients;*

[receiving by a computer dispensing data including which at least one medication was actually dispensed to a patient;]

processing, on a computer [the received], dispensing data *received from each of the plurality of pharmaceutical storage and electronic dispensing carts* so that only medication actually dispensed is to be billed;

processing, on a computer, billing records including billing data for each of the plurality of patients at each of the plurality of long-term care facilities based on the received dispensing data, the billing data including *a* reimbursement provider;

consolidating the billing data according to *the* reimbursement provider to thereby generate reimbursements from one or more reimbursement providers, the billing data also including [billing] data for *indicating* medications actually dispensed to a respective patient from at least one of the plurality of pharmaceutical storage and electronic dispensing carts so that only medication actually dispensed is billed to the reimbursement provider; and submitting separate consolidated reimbursement claims from a computer to each respective reimbursement provider.

9. A computer implemented method as defined in claim 8, wherein the step of consolidating billing data by reimbursement provider further includes consolidating billing data by patient at a patient care facility for each reimbursement provider.

10. A computer implemented method as defined in claim 9, [wherein the step of receiving dispensing data further includes] *further comprising: receiving* dispensing data of medications remaining stored in bulk in and not actually dispensed from a pharmaceutical storage and electronic dispensing cart.

11. A computer implemented method as defined in claim 8, further comprises submitting from the computer consolidated reimbursement claims for each patient to a patient representative.

12. A computer implemented method as defined in claim 8, wherein the step of [processing control data] *dispensing* includes dispensing the packaged *one of the plurality of individual patient dosing packages containing the* at least one medication into [the] *a* container *separable from the cart* during [the] *a* preselected time [intervals] *interval* prior to a predetermined schedule of distribution of medication dosages to the plurality of patients in each of the patient care facilities, and wherein the step of consolidating billing data by reimbursement provider includes consolidating billing data by reimbursement provider for each of a plurality of patients at a patient care facility.

13. A computer implemented method as defined in claim 8, wherein the step of consolidating billing data further includes consolidating billing data by long term care facility for each reimbursement provider.

14. A computer implemented method as defined in claim 8, wherein the consolidating step comprises consolidating billing data from a remote pharmacy, and wherein the consolidating step includes consolidating billing data with a plurality of additional billing data from a plurality of additional remote pharmacies.

15. [A] *One or more non-transitory computer readable media having tangibly embodied thereon* computer readable pharmacy management program [product stored on one or more tangible computer readable storage media] *code*, the pharmacy management program [product] *code* comprising a set of instructions that when executed by one or more computers, cause the one or more computers to perform the following operations:

[scheduling one or more preselected time intervals for dispensing of at least one medication according to patient specific prescription requirements through each of a plurality of pharmaceutical storage and electronic dispensing carts, each of the plurality of pharmaceutical storage and electronic dispensing carts having a plurality of different medications stored in bulk therein;] *scheduling a dispensing of at least one medication of a plurality of medications stored in bulk on one of a plurality of pharmaceutical storage and electronic dispensing carts located at a plurality of long term care facilities, the dispensing performed through the one of a plurality of pharmaceutical storage and electronic dispensing carts according to patient specific prescription requirements;* processing control data by each of the plurality of pharmaceutical storage and electronic dispensing carts to [individually] retrieve *the* at least one medication of the plurality of different medications [stored in bulk], load the at least one medication into one of [the] *a* plurality of disposable individual patient dosing packages, package the at least one medication, and dispense the loaded and packaged one of the plurality of individual patient dosing packages [into a container associated with the cart to thereby have dispensed medication distributed by authorized medical personnel according to the patient specific prescription requirements after separating the container from the cart when having the loaded and packaged one of the plurality of individual patient dosing packages therein;] *for distribution by authorized medical personnel according to the patient specific prescription requirements;* receiving dispensing data including which at least one medication was actually dispensed to a patient;

processing the received dispensing data so that only medication actually dispensed is to be billed;

processing separate billing record data including billing data for each of the plurality of patients at each of the plurality of long-term care facilities based on the received dispensing data, the billing data being indexed by *a* reimbursement provider;

consolidating the billing data according to *the* reimbursement provider to thereby generate reimbursements from one or more reimbursement providers, the billing data also including [billing] data [for] *indicating* medications actually dispensed to a respective patient from at least one of the plurality of pharmaceutical storage and electronic dispensing carts so that only medication actually dispensed is billed to the reimbursement provider; and submitting separate consolidated reimbursement claims to each respective reimbursement provider.

16. [Pharmacy management program product] *The one or more computer readable media* as defined in claim 15, wherein the operation of processing control data includes dispensing the packaged at least one medication into [the] *a* container during preselected time intervals prior to a predetermined schedule of distribution of medication dosages to the plurality of patients in each of a plurality of patient care facilities.

17. [Pharmacy management program product] *The one or more computer readable media* as defined in claim [16] *15*, *wherein* the operation of receiving dispensing data further includes dispensing data of medications remaining stored in bulk in and not actually dispensed from a pharmaceutical storage and electronic dispensing cart.

18. [Pharmacy management program product] *The one or more computer readable media* as defined in claim 15, wherein the operations further comprise submitting consolidated reimbursement claims for each patient to a patient representative.

19. [Pharmacy management program product] *The one or more computer readable media* as defined in claim 15, wherein the operation of consolidating billing data by reimbursement provider further includes the operation of consolidating billing data by patient for each reimbursement provider, and wherein the operation of submitting consolidated reimbursement claims includes electronically submitting the consolidated reimbursement claims to each respective reimbursement provider for each associated patient in batch format.

20. [Pharmacy management program product] *The one or more computer readable media* as defined in claim 15, wherein the operation of consolidating billing data further includes the operation of consolidating billing data by patient care facility for each reimbursement provider.

21. [Pharmacy management program product] *The one or more computer readable media* as defined in claim 15, wherein the [pharmacy management program product is adapted to provide instructions for the operation of] *operations further comprise* consolidating billing data with a plurality of additional billing data from a plurality of remote pharmacies.

22. [A] *One or more non-transitory computer readable storage media having tangibly embodied thereon* computer readable pharmacy management program [product stored on one or more tangible computer readable storage media] *code*, the pharmacy management program [product] *code* comprising a set of instructions that when executed by one or more computers, cause the one or more computers to perform the following operations:

[scheduling one or more preselected time intervals for dispensing of at least one medication according to patient specific prescription requirements through each of a plurality of pharmaceutical storage and electronic dispensing carts, each of the plurality of pharmaceutical storage and electronic dispensing carts having a plurality of different medications stored in bulk therein and being located at a different long term care facility;] *scheduling a dispensing of at least one medication of a plurality of medications stored in bulk on one of a plurality of pharmaceutical storage and electronic dispensing carts located at a plurality of long term care facilities, the dispensing performed through the one of a plurality of pharmaceutical storage and electronic dispensing carts according to patient specific prescription requirements;* controlling each of the plurality of pharmaceutical storage and electronic dispensing carts to [individually] retrieve *the* at least one medication of the plurality of [different] medications [stored in bulk], load the at least one medication into one of [the] *a* plurality of disposable individual patient dosing packages, package the at least one medication, and dispense the loaded and packaged one of the plurality of individual patient dosing packages [into a container associated with the cart to thereby have dispensed medication distributed by authorized medical personnel according to the patient specific prescription requirements after separating the container from the cart when having the loaded and packaged one of the plurality of individual patient dosing packages therein;] *for distribution by authorized medical personnel according to patient specific prescription requirements;* receiving dispensing data including which at least one medication was actually dispensed to a patient;

processing the received dispensing data so that only medication actually dispensed is to be billed;

processing billing records based on medication dispensing data received from each of the plurality of pharmaceutical storage and electronic dispensing carts, the billing records including billing data for each of [the] *a* plurality of patients at each of the plurality of long-term care facilities, the billing data for each long-term care patient being indexed by *a* reimbursement provider;

consolidating the billing data according to *the* reimbursement provider to thereby generate reimbursements from one or more reimbursement providers, the billing data also including [billing] data for *indicating* medications actually dispensed to a respective patient from at least one of the plurality of pharmaceutical storage and electronic dispensing carts so that only medication actually dispensed is billed to the reimbursement provider; and submitting separate consolidated reimbursement claims to each respective reimbursement provider.

23. [Pharmacy management program product] *The one or more computer readable media* as defined in claim 22, wherein the billing data for each patient is indexed by reimbursement provider, wherein the operation of consolidating billing data by reimbursement provider includes the operation of consolidating billing data by reimbursement provider for each of a plurality of patients at the long term care facility.

24. [Pharmacy management program product] *The one or more computer readable media* as defined in claim 22, *wherein* the operation of receiving dispensing data further includes dispensing data of medications remaining stored in bulk in and not actually dispensed from a pharmaceutical storage and electronic dispensing cart.

25. [Pharmacy management program product] *The one or more computer readable media* as defined in claim 22, wherein the operation of consolidating billing data by reimbursement provider further includes the operation of consolidating billing data by patient for each reimbursement provider, and wherein the operation of submitting consolidated reimbursement claims includes electronically submitting the consolidated reimbursement claims to each respective reimbursement provider for each associated patient in batch format.

26. [Pharmacy management program product] *The one or more computer readable media* as defined in claim 22, wherein the operations further comprise submitting consolidated reimbursement claims for each patient to a patient representative.

27. [Pharmacy management program product] *The one or more computer readable media* as defined in claim 22, wherein the [pharmacy management program product is adapted to provide instructions for the operation of] *operations further comprise* consolidating billing data for medications dispensed to a plurality of patients from a plurality of pharmaceutical storage and electronic dispensing carts, and wherein at least one of the plurality of pharmaceutical storage and electronic dispensing carts is located at a long term care facility different than another long term care facility.

28. [Pharmacy management program product] *The one or more computer readable media* as defined in claim 22, wherein the [pharmacy management program product is adapted to provide instructions for the operation of] *operations further comprise* consolidating billing data with a plurality of additional billing data from a plurality of additional remote pharmacies.

* * * * *